United States Patent
Wada et al.

(10) Patent No.: US 8,288,527 B2
(45) Date of Patent: Oct. 16, 2012

(54) OLIGO-AMINOSACCHARIDE COMPOUND

(75) Inventors: Takeshi Wada, Chiba (JP); Rintaro Iwata, Chiba (JP)

(73) Assignee: The University of Tokyo, Tokyo (JP)

( * ) Notice: Subject to any disclaimer, the term of this patent is extended or adjusted under 35 U.S.C. 154(b) by 326 days.

(21) Appl. No.: 12/659,425

(22) Filed: Mar. 9, 2010

(65) Prior Publication Data

US 2011/0003980 A1 Jan. 6, 2011

Related U.S. Application Data

(60) Provisional application No. 61/159,157, filed on Mar. 11, 2009.

(30) Foreign Application Priority Data

Mar. 10, 2009 (JP) ................................ 2009-056885

(51) Int. Cl.
 *C08B 37/00* (2006.01)
 *C07H 5/04* (2006.01)
 *C07H 5/06* (2006.01)
(52) U.S. Cl. .................... 536/55.2; 536/18.7; 536/123.1
(58) Field of Classification Search .................. None
 See application file for complete search history.

(56) References Cited

OTHER PUBLICATIONS

International Preliminary Report on Patentability for PCT/JP2010/054282, mailed Sep. 22, 2011 (English and Japanese).
Wada et al., 88th Annual Convention of Chemical Society of Japan, 2C6-03, p. 897, Abstract published on the Web site Mar. 12, 2008.
Iwatani et al., 89th Annual Convention of Chemical Society of Japan, 2 H6-32, p. 1274, Abstract published on the Web site Mar. 13, 2009.
Iwata et al., Nucleic Acids Symposium Series, Sep. 27, 2009, No. 53, pp. 113-114.
Fourmy et al., Science, 1996, vol. 274, pp. 1367-1371.
Freisz et al., Angewandte Chemie International Edition, 2008, vol. 47, Iss. 22, pp. 4110-4113.
Fourmy et al., Journal of Molecular Biology, 1998, vol. 277, Iss. 2, p. 347-362.
Venot et al., ChemBioChem, 2004, vol. 5, Iss. 9, pp. 1228-1236.
International Search Report and International Search Opinion issued in connection with the counterpart International Application PCT/JP2010/05428, dated Apr. 20, 2010.

*Primary Examiner* — Patrick Lewis
(74) *Attorney, Agent, or Firm* — Greenblum & Bernstein, P.L.C.

(57) ABSTRACT

An oligo-aminosaccharide compound formed by binding 3 to 6 saccharides, such as 2,6-diamino-2,6-dideoxy-$\alpha$-(1$\rightarrow$4)-D-glucopyranose oligomers, or a salt thereof, which has high affinity to a double-stranded nucleic acid.

7 Claims, 10 Drawing Sheets
(10 of 10 Drawing Sheet(s) Filed in Color)

(A)

(B)

(C)

(A)

(B)

(A)

(B)

(A)

(B)

(A)

(B)

(A)

(B)

SEQUENCE LISTING

```
<160> NUMBER OF SEQ ID NOS: 9

<210> SEQ ID NO 1
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
aaaaaauuuu uu                                                          12

<210> SEQ ID NO 2
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
aaaaaaaaaa aa                                                          12

<210> SEQ ID NO 3
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
aaaaaaaaaa aaaaaaaaaa aaaa                                             24

<210> SEQ ID NO 4
<211> LENGTH: 12
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 4
aaaaaaaaaa aa                                                              12

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
aaaaaaaaaa aaaaaaaaaa aaaa                                                 24

<210> SEQ ID NO 6
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
cgcgaauucg cg                                                              12

<210> SEQ ID NO 7
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
aacccgcggg uu                                                              12

<210> SEQ ID NO 8
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
cgcgaattcg cg                                                              12

<210> SEQ ID NO 9
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
aacccgcggg tt                                                              12
```

OLIGO-AMINOSACCHARIDE COMPOUND

CROSS-REFERENCE TO RELATED APPLICATIONS

This application claims the benefit of U.S. Provisional Application No. 61/159,157, filed Mar. 11, 2009.

TECHNICAL FIELD

The present invention relates to an oligo-aminosaccharide compound having a property of binding to an RNA double-stranded nucleic acid or a DNA/RNA double-stranded nucleic acid, but not binding to a DNA double-stranded nucleic acid.

BACKGROUND ART

It is known that DNAs responsible for storage of genetic information and RNAs having various functions as transcripts of DNAs interact with biomolecules such as proteins, various small organic molecules, saccharide compounds, metal ions, and the like. As the saccharide compounds that can interact with DNAs and RNAs, for example, the following compounds are known. Most of these compounds bind to a nucleic acid molecule as an intercalator where an aromatic ring in the molecule is inserted between base pairs of a DNA double-stranded nucleic acid or a DNA/RNA double-stranded nucleic acid.

[Formula 1]

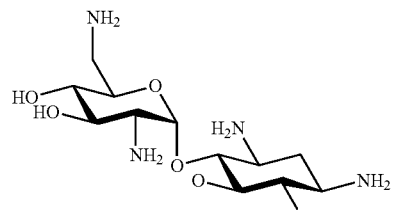

Neamine

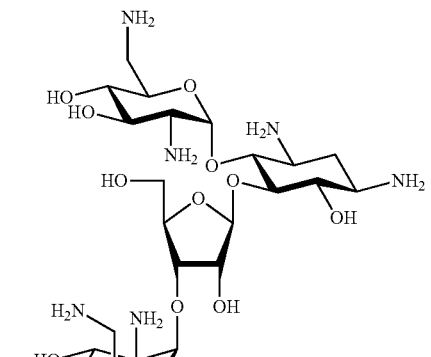

Neomycin B

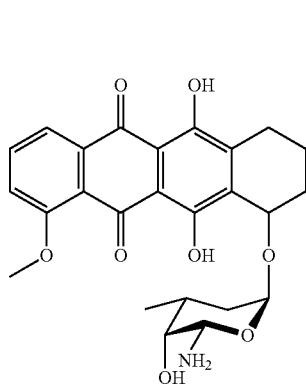

Daunorubicin (R = H)
Doxorubicin (R = OH)

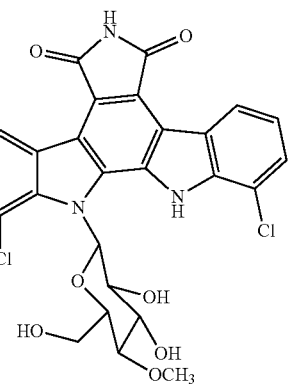

Rebeccamycin

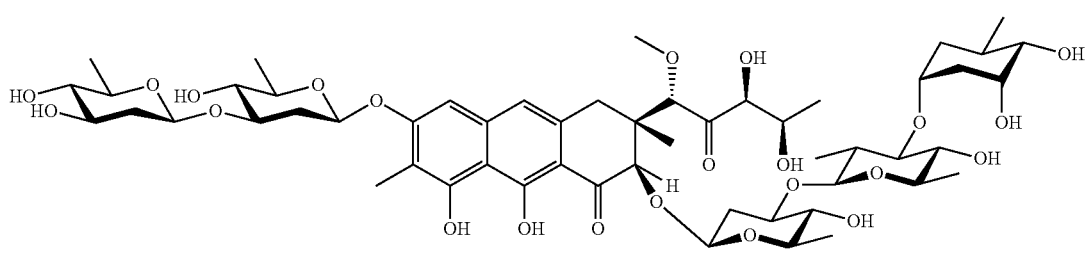

Mithramycin

Saccharide derivatives include aminoglycoside antibiotics such as neamine and neomycin B mentioned above, of which functional group deriving from saccharide primarily participates in binding with nucleic acids. These molecules were known for a long time to site-specifically bind to bacterial 16S rRNA. Recently, it has been revealed that they interact with various RNAs such as the Tat region and Rev region of HIV, and RNA double helices. Further, X-ray crystallography of aminoglycosides suggests that amino group and hydroxyl group of aminoglycosides interact with a phosphate moiety and a base moiety of a nucleic acid (Science, 274, pp. 1367-1371, 1996; J. Mol. Biol., 277, pp. 347-362, 1998; Angew. Chem. Int. ed., 47, pp. 4110-4113, 2008).

It has recently been suggested that oligo-2,6-diamino-2,6-deoxy-α-glucopyranosides having an α-glycosidic linkage may bind to a DNA double-stranded nucleic acid (89th Annual Convention of Chemical Society of Japan, Subject number 2C6-03, Abstract was published on the WEB site on Mar. 13, 2008). As for these oligo-diaminosaccharide compounds, it has been suggested that they are expected to have a strong interaction with the negative charge of the phosphate moieties in both ends of the DNA at binding to a major groove, because they have amino groups at both ends of the molecule and the amino groups are protonated under a physiological condition to form a dication, and that they can easily form a curved structure, which is entropically advantageous at binding to a DNA major groove, because they have a structure in which all of the saccharides are linked via α-glycosidic linkages. However, only up to an intermediate compound in the synthetic route of trisaccharide was actually reported as synthesis thereof. Further, any experimental results as for interactions of these compounds with DNAs were not reported, and the report fails to teach or suggest whether the compounds have affinity also to an RNA double-stranded nucleic acid or a DNA/RNA double-stranded nucleic acid.

PRIOR ART REFERENCES

Non-Patent Documents

Non-patent document 1: Science, 274, pp. 1367-1371, 1996
Non-patent document 2: J. Mol. Biol., 277, pp. 347-362, 1998
Non-patent document 3: Angew. Chem. Int. ed., 47, pp. 4110-4113, 2008
Non-patent documents 4: 89th Annual Convention of Chemical Society of Japan,
Subject number 2C6-03, Abstract published on the WEB site on Mar. 13, 2008

SUMMARY OF THE INVENTION

Object to be Achieved by the Invention

An object of the present invention is to provide a saccharide compound which has affinity to a nucleic acid. More specifically, the object of the present invention is to provide an oligo-aminosaccharide compound which has strong affinity to a double-stranded nucleic acid.

Means for Achieving the Object

The inventors of the present invention conducted various researches on the oligo-2,6-diamino-2,6-deoxy-α-glucopyranosides mentioned above having the α-glycosidic linkages, and prepared the trisaccharide compound and tetrasaccharide compound thereof. As a result, they surprisingly found that these saccharide compounds did not substantially bind to a DNA double-stranded nucleic acid, whilst selectively bound only to an RNA double-stranded nucleic acid or a DNA/RNA double-stranded nucleic acid. They also found that the disaccharide compound specifically described in the aforementioned publication failed to substantially bind to a double-stranded nucleic acid, and also failed to substantially bind to an RNA double-stranded nucleic acid or a DNA/RNA double-stranded nucleic acid. The present invention was accomplished on the basis of these findings.

The present invention thus provides a compound represented by the following general formula (I):

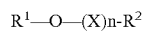

wherein $R^1$ represents hydrogen atom or a monovalent substituent, $R^2$ represents hydrogen atom or a monovalent substituent, n represents an integer of 3 to 6, and n of the groups X may be the same or different, and are independently selected from the divalent groups represented by the following formulas (a) to (i):

[Formula 2]

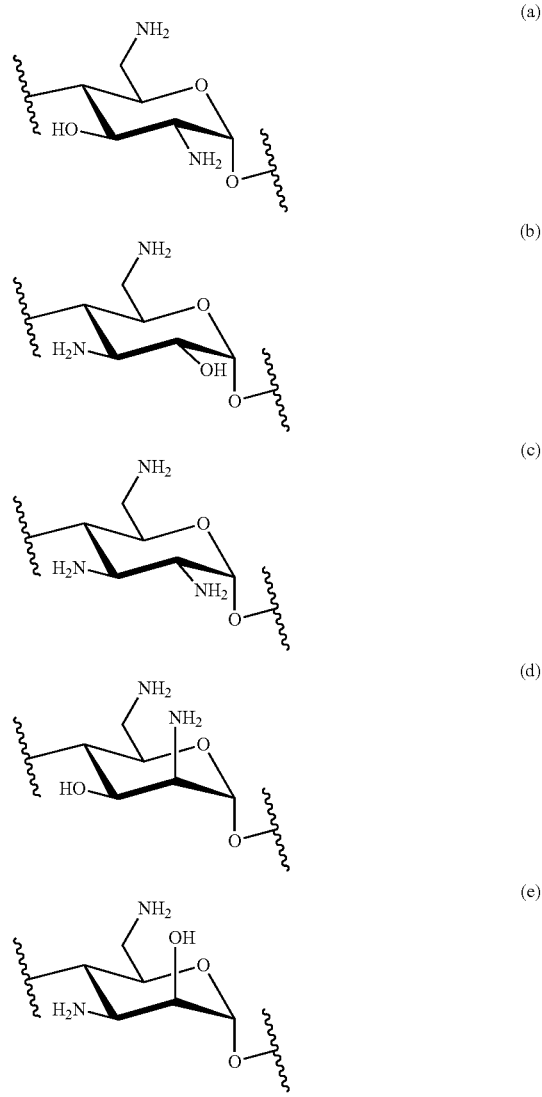

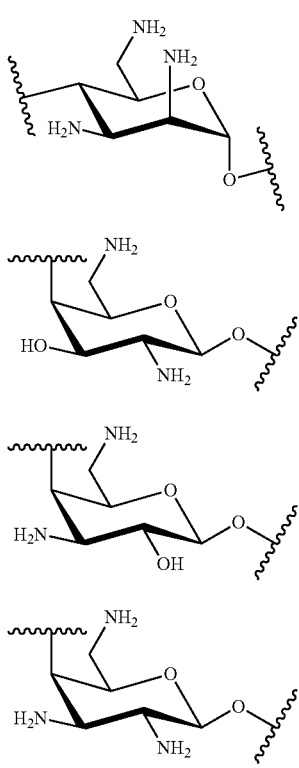

or a salt thereof.

According to preferred embodiments of the present invention, there are provided the aforementioned compound or a salt thereof, wherein $R^1$ is hydrogen atom; the aforementioned compound or a salt thereof, wherein $R^2$ is hydrogen atom or an alkyl group which may have a substituent; the aforementioned compound or a salt thereof, wherein X is a divalent group represented by any one of the formulas (a) to (f); the aforementioned compound or a salt thereof, wherein n of the groups X all represent the divalent group represented by the formula (a); and the aforementioned compound or a salt thereof, wherein n is 3 or 4.

From other aspects, there are provided an agent for stabilizing an A-type double-stranded nucleic acid, which comprises a compound represented by the aforementioned general formula (I) or a salt thereof the aforementioned stabilizing agent, wherein the A-type double-stranded nucleic acid is an RNA double-stranded nucleic acid or a DNA/RNA double-stranded nucleic acid; a method for stabilizing an A-type double-stranded-nucleic acid, which comprises the step of contacting a compound represented by the aforementioned general formula (I) or a salt thereof with the A-type double-stranded nucleic acid; and the aforementioned stabilizing method, wherein the A-type double-stranded nucleic acid is an RNA double-stranded nucleic acid or a DNA/RNA double-stranded nucleic acid.

From a still further aspect, there are provided an agent for selectively binding to an A-type double-stranded nucleic acid, which comprises a compound represented by the aforementioned general formula (I) or a salt thereof, and the aforementioned binding agent, wherein the A-type double-stranded nucleic acid is an RNA double-stranded nucleic acid or a DNA/RNA double-stranded nucleic acid. By binding a desired substance to the aforementioned binding agent, for example, an active ingredient of a medicament such as anti-tumor agents and antibacterial agents, nucleic acids, saccharides, lipids, proteins, peptides, and metallic compounds, the substance can be selectively delivered to an A-type double-stranded nucleic acid.

The present invention also provides a complex of a compound represented by the aforementioned general formula (I) or a salt thereof and an A-type double-stranded nucleic acid. According to a preferred embodiment, a complex of a compound represented by the aforementioned general formula (I) or a salt thereof and an RNA double-stranded nucleic acid or a DNA/RNA double-stranded nucleic acid is provided.

Effect of the Invention

The compound or a salt thereof of the present invention does not substantially bind to a DNA double-stranded nucleic acid having the B-type helical structure, whilst can selectively bind to an RNA double-stranded nucleic acid or DNA/RNA double-stranded nucleic acid having the A-type helical structure in a physiological environment. Therefore, the compound or a salt thereof of the present invention can be used as an agent for stabilizing an A-type double-stranded nucleic acid, and by binding the compound of the present invention to another substance such as an active ingredient of a medicament and a nucleic acid, the active ingredient of a medicament or the nucleic acid can be selectively delivered to an A-type double-stranded nucleic acid.

BRIEF EXPLANATION OF THE DRAWINGS

The patent or application file contains at least one drawing executed in color. Copies of this patent or patent application publication with color drawing(s) will be provided by the Office upon request and payment of the necessary fee.

Figure 1:
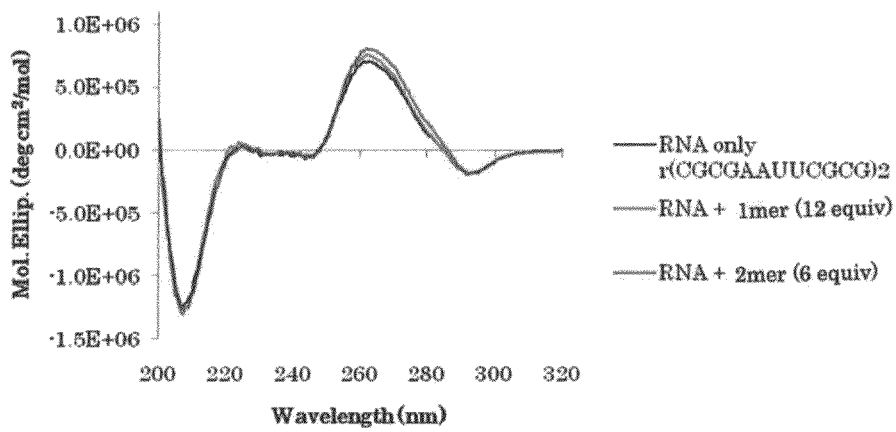
FIGS. 1A-C depict CD spectra of RNA (I) (SEQ ID NO: 6).
Figure 1:
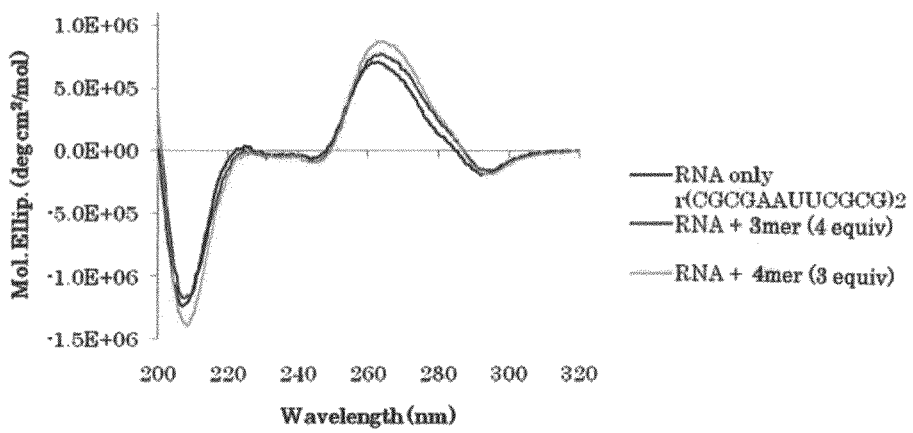
Figure 1:
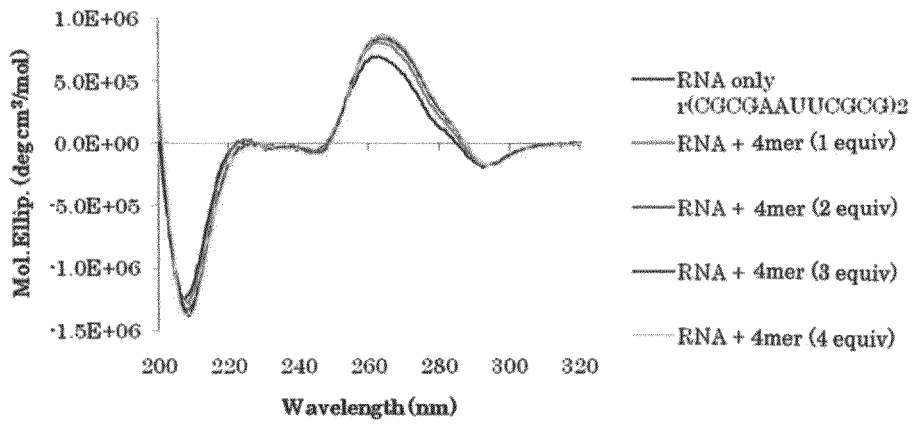

MODE FOR CARRYING OUT THE INVENTION $R^1$ represents hydrogen atom or a monovalent substituent. Examples of the monovalent substituent include, for example, an alkyl group which may have a substituent, and the like. However, the monovalent substituent is not limited to an alkyl group, and any monovalent substituents can be used. As the alkyl group represented by $R^1$, a linear, branched or cyclic alkyl group, or an alkyl group consisting of such alkyl groups may be used, and the carbon number thereof is, for example, about 1 to 20, preferably about 1 to 12, more preferably about 1 to 8, and most preferably about 1 to 6. The alkyl group may contain one or two or more the same or different heteroatoms (oxygen atom, nitrogen atom, sulfur atom and the like) in the carbon chain as chain-constituting atoms. The alkyl group may have one or two or more substituents. Examples of the substituent of the alkyl group include, for example, hydroxyl group, an alkoxyl group, a halogen atom (fluorine atom, chlorine atom, bromine atom or iodine atom), amino group, a monoalkylamino group, a dialkylamino group, carboxyl group, an alkoxycarbonyl group, oxo group, sulfo group, and the like, but it is not limited to these examples. As $R^1$, hydrogen atom is preferred.

$R^2$ represents hydrogen atom or a monovalent substituent. As the monovalent substituent, those explained for $R^1$ can be used. $R^2$ preferably represents hydrogen atom or an alkyl group, more preferably an alkyl group, still more preferably an alkyl group having about 1 to 6 carbon atoms. Methyl group can be most preferably used.

Symbol n represents an integer of 3 to 6, and n of the groups X may be the same or different, and independently represent a divalent group selected from the group consisting of those represented by the aforementioned formulas (a) to (i). All of n of the groups X may represent the same divalent group. For example, where n of the divalent groups represented by the formula (a) bind, the compound is 2,6-diamino-2,6-dideoxy-α-(1→4)-D-glucopyranose oligomer, where n of the divalent groups represented by the formula (b) bind, the compound is 3,6-diamino-3,6-dideoxy-α-(1→4)-D-glucopyranose oligomer, where n of the divalent groups represented by the formula (d) bind, the compound is 2,6-diamino-2,6-dideoxy-α-(1→4)-D-mannopyranose oligomer, and where n of the divalent groups represented by the formula (e) bind, the compound is 3,6-diamino-3,6-dideoxy-α-(1→4)-D-mannopyranose oligomer. Further, where n of the divalent groups represented by the formula (g) bind, the compound is 2,6-diamino-2,6-dideoxy-β-(1→4)-D-galactopyranose oligomer, and where n of the divalent groups represented by the formula (h) bind, the compound is 3,6-diamino-3,6-dideoxy-β-(1→4)-D-galactopyranose oligomer. The divalent group is preferably selected from the group consisting of the groups represented by the formulas (a) to (f), more preferably selected from the group consisting of the groups represented by the formulas (a), (b), (d) and (e), still more preferably selected from the group consisting of the groups represented by the formulas (a) and (d). It is particularly preferred that all n of the groups X are the divalent groups represented by the formula (a), or all n of the groups X are the divalent groups represented by the formula (d), and it is most preferred that all n of the groups X are the divalent groups represented by the formula (a).

Among the compounds of the present invention represented by aforementioned general formula (I), for example, the compounds wherein all n of the groups X are the divalent groups represented by the formula (a) can be prepared by repeating the step of reacting a compound serving as a glycosyl donor with a compound serving as a glycosyl acceptor to prepare an α-anomer an appropriate number of times. For example, a compound to which a desired number n of the groups represented by the formula (a) bind can be prepared by repeating the following cycle (in the scheme, Phth represents phthaloyl group, Bn represents benzyl group, Ac represents acetyl group, Me represents methyl group, and Ph represents phenyl group). For the compounds having a group or groups other than the group represented by the formula (a) as X, the reaction can be carried out in a similar manner. A method for synthesizing a compound represented by the aforementioned general formula (I) of the present invention wherein four of divalent groups represented by the formula (a) are bound is specifically shown in Examples of the specification. Therefore, those skilled in the art can easily prepare any compounds of the present invention falling within the scope of the general formula (I) by referring to the aforementioned general descriptions and specific descriptions in the examples with suitably choosing starting materials, reaction reagents, protective groups, reaction conditions, and the like.

[Formula 3]
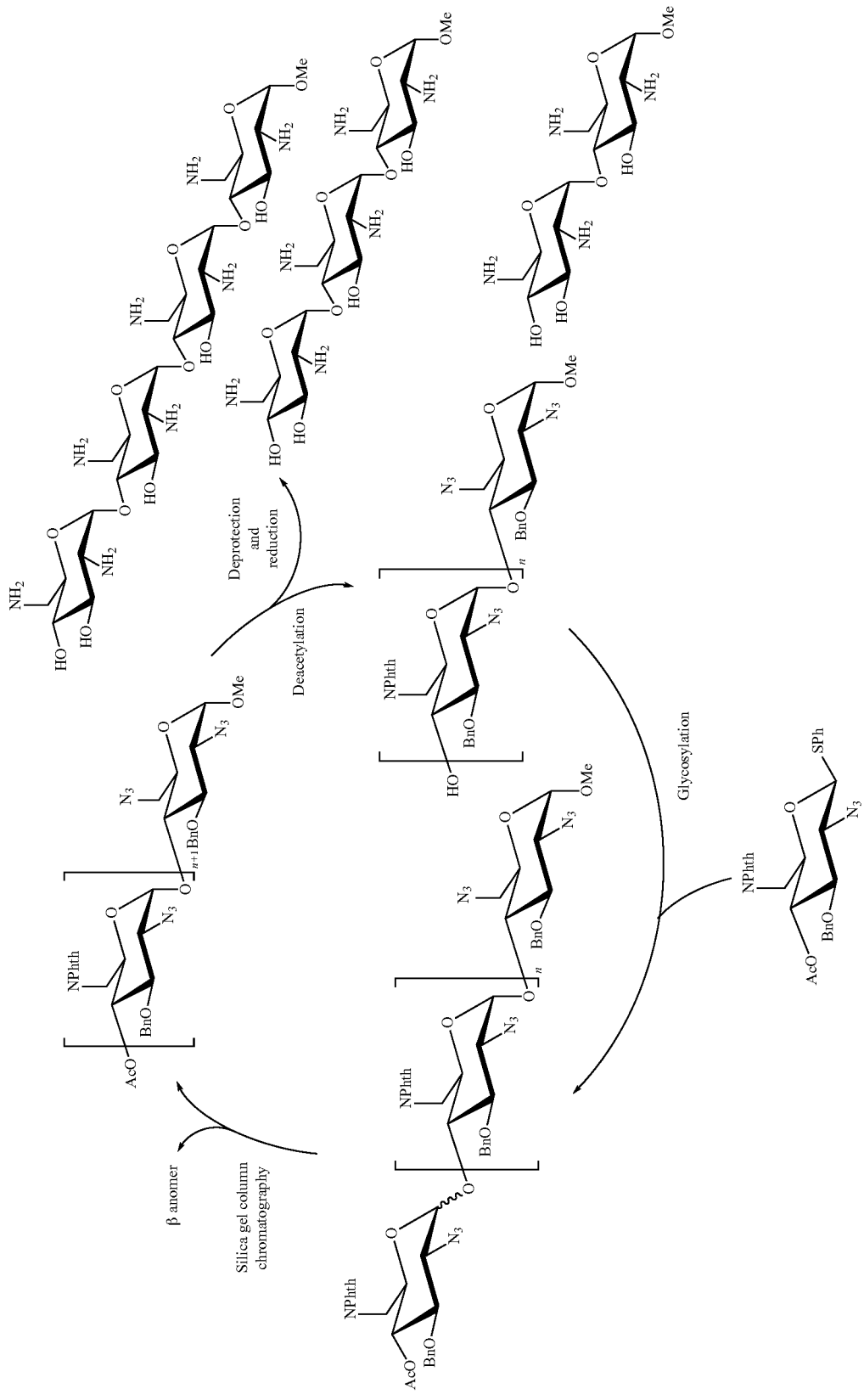

The compounds represented by the general formula (I) may form a salt. As the salt, an acid addition salt is generally formed, and the acid may be any of mineral acids such as hydrochloric acid, sulfuric acid and nitric acid, and organic acids such as maleic acid, tartaric acid, malic acid, p-toluenesulfonic acid and methanesulfonic acid. The salt is preferably a salt of a mineral acid such as hydrochloric acid. The compounds represented by the general formula (I) and salts thereof may form a hydrate or a solvate, and it should be understood that these substances fall within the scope of the present invention.

The compounds of the present invention represented by the general formula (I) have a property that they can bind to a major groove of an RNA double-stranded nucleic acid and a DNA/RNA double-stranded nucleic acid, whilst they do not bind to a major groove of a DNA double-stranded nucleic acid. It is known that RNA double-stranded nucleic acids and DNA/RNA double-stranded nucleic acids have the A-type double helix structure under a physiological condition, and that DNA double-stranded nucleic acids have the B-type double helix structure having a wide major groove under a physiological condition. The compounds of the present invention represented by general formula (I) have a property that they can selectively bind to a double-stranded nucleic acid having the A-type double helix structure (referred to herein as "A-type double-stranded nucleic acid"). Further, the compounds of the present invention represented by general formula (I) have an action of selectively binding to an A-type double-stranded nucleic acid, for example, an RNA double-stranded nucleic acid or a DNA/RNA double-stranded nucleic acid to stabilize the A-type double-stranded nucleic acid by the binding. Therefore, the compounds of the present invention represented by general formula (I) can be used as an agent for stabilizing an A-type double-stranded nucleic acid. For example, they can stabilize a complex of siRNA or antisense RNA, which has a gene expression control function, and RNA or DNA, and can enhance the function of such RNA.

Furthermore, the compounds of the present invention represented by general formula (I) bind to an A-type double-stranded nucleic acid, whilst do not substantially bind to a double-stranded nucleic acid having the B-type double helix structure (referred to herein as "B-type double-stranded nucleic acid"). Therefore, an A-type double-stranded nucleic acid and a B-type double-stranded nucleic acid can be distinguished by using the compounds of the present invention. From this viewpoint, the compounds of the present invention can be used as an agent selectively binding to an A-type double-stranded nucleic acid. Thus, for example, by binding a desired substance, for example, an active ingredient of a medicament such as antitumor agents and antibacterial agents, nucleic acids, saccharides, lipids, proteins, peptides, and metallic compounds, to the compound of the present invention, the substance can be selectively delivered to an A-type double-stranded nucleic acid.

EXAMPLES

The present invention will be more specifically explained with reference to examples. However, the scope of the present invention is not limited to the following examples. In the examples, the symbols have the following meanings: Ac: acetyl group, Bn: benzyl group, DMAP: dimethylaminopyridine, Ms: methanesulfonyl group, NIS: N-iodosuccinimido group, NPCC: p-nitrophenoxycarbonyl chloride, Phth: phthaloyl group, PMB: p-methoxybenzyl group, PMP: p-methoxyphenyl group, Tf: trifluoromethanesulfonyl group, TFA: trifluoroacetic acid, TMS: trimethylsilyl group, and Ts: p-toluenesulfonyl group.

Example 1

According to the following synthetic schemes, glycosyl donor compounds and glycosyl acceptor compounds were prepared, and from the α-anomers obtained by binding the resulting compounds, disaccharide compounds, trisaccharide compounds, and tetrasaccharide compounds were prepared.

[Formula 4]

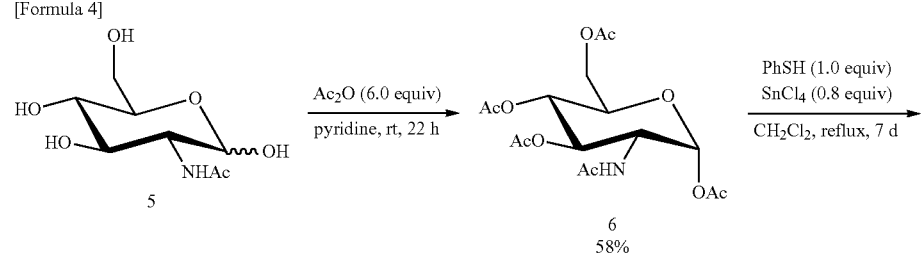

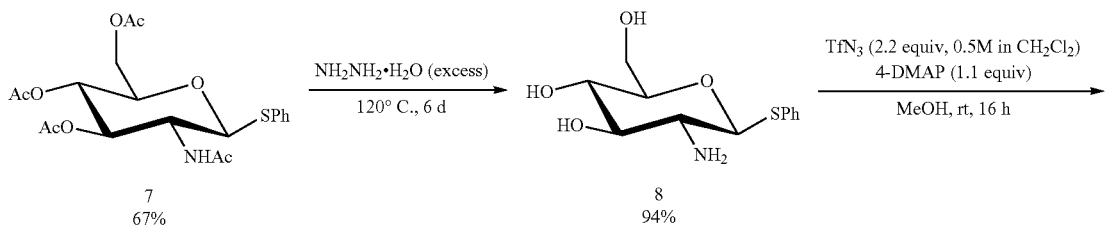

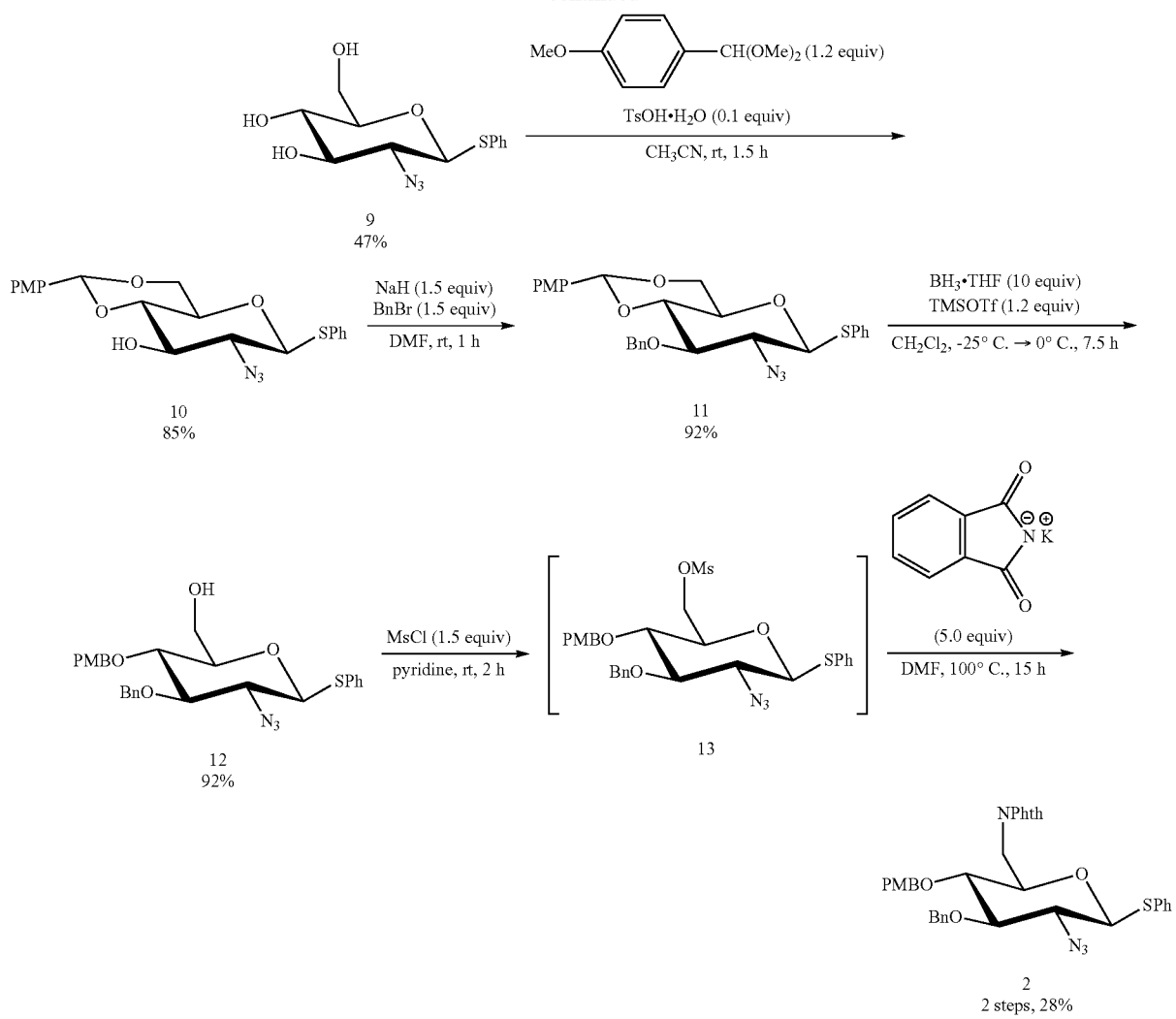
[Formula 5]
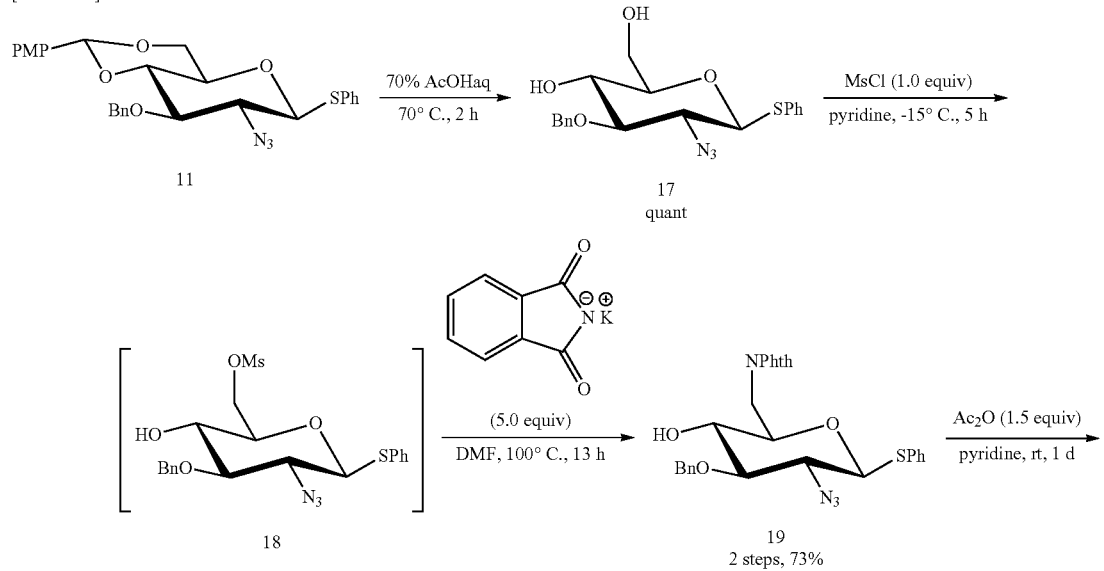

-continued
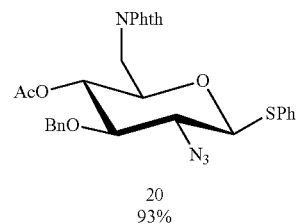
[Formula 6]
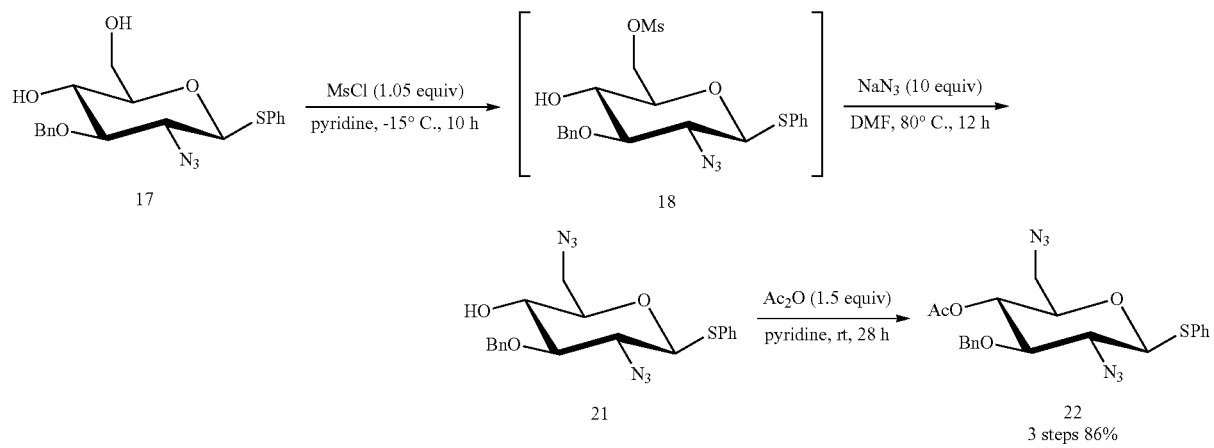
[Formula 7]
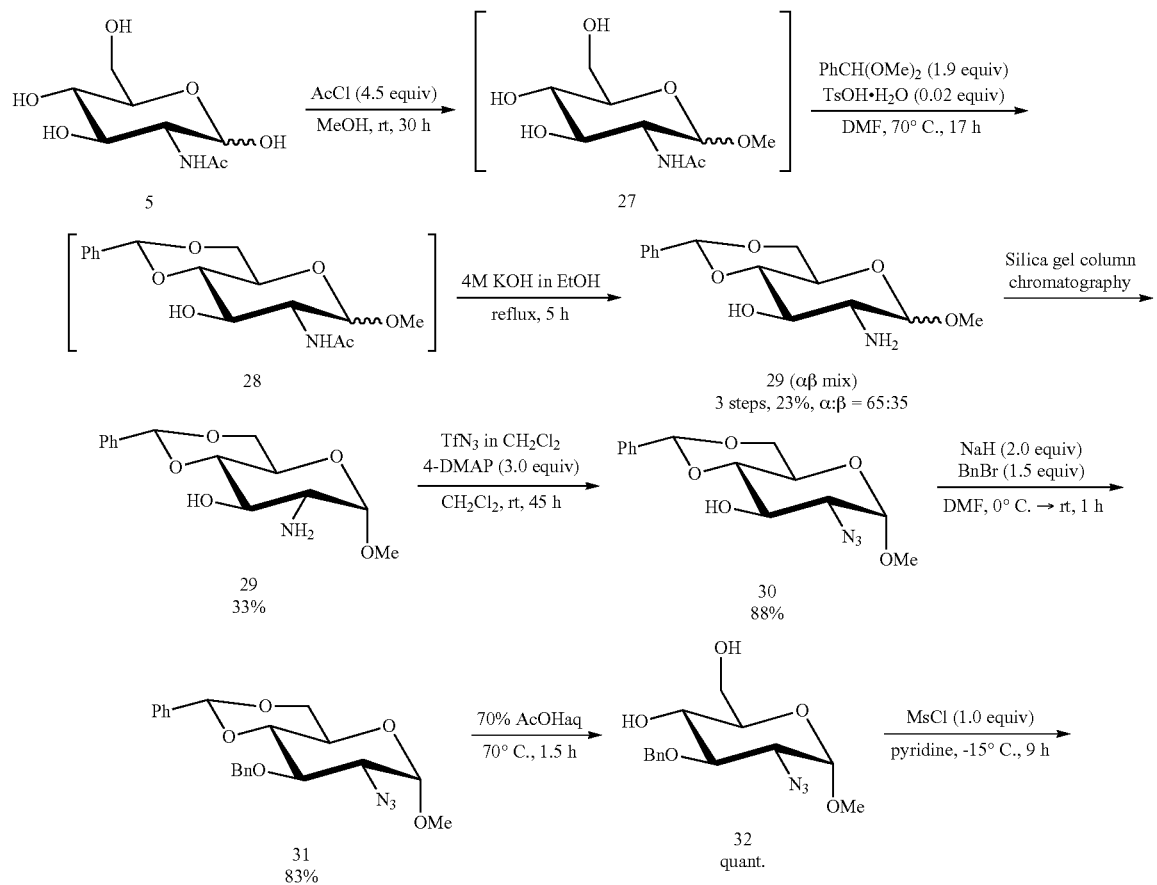

-continued
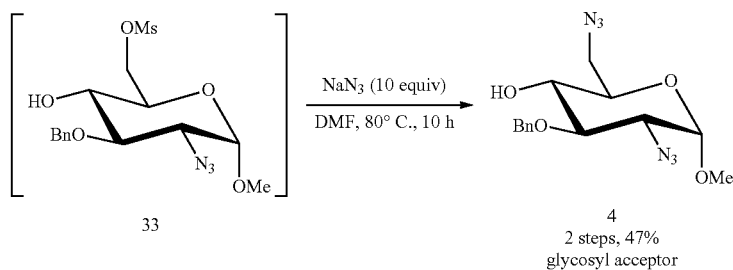
33
4
2 steps, 47%
glycosyl acceptor
[Formula 8]
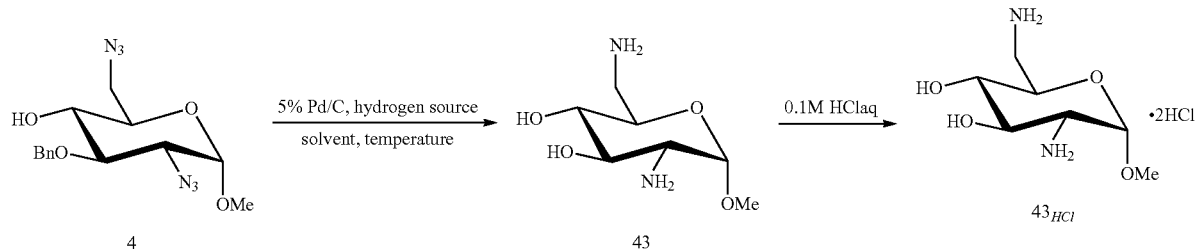
4
43
43$_{HCl}$
[Formula 9]
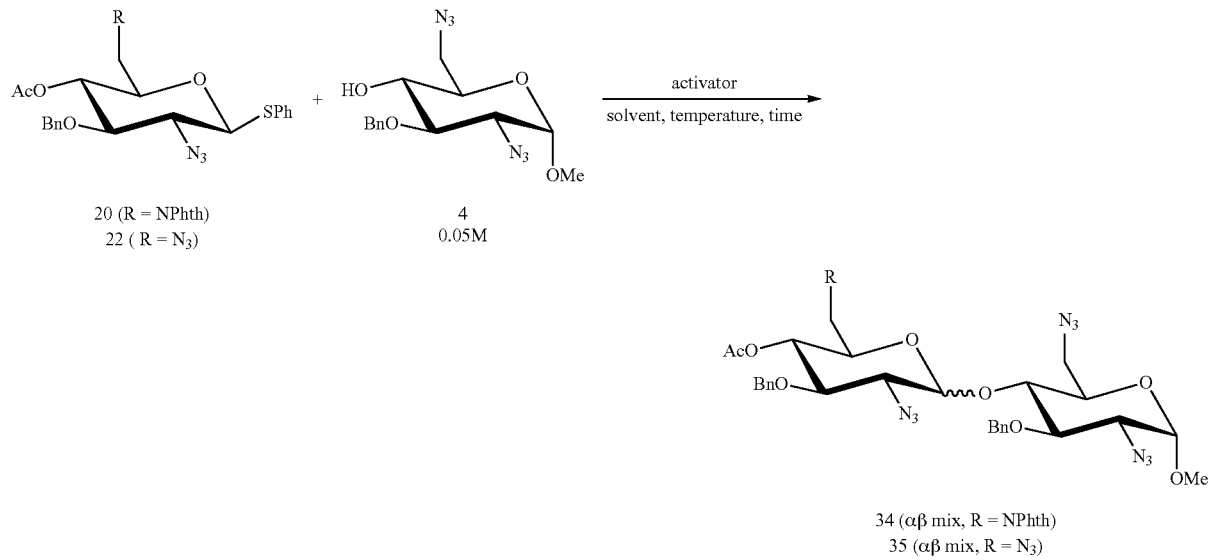
20 (R = NPhth)
22 (R = N$_3$)
4
0.05M
34 (αβ mix, R = NPhth)
35 (αβ mix, R = N$_3$)
[Formula 10]
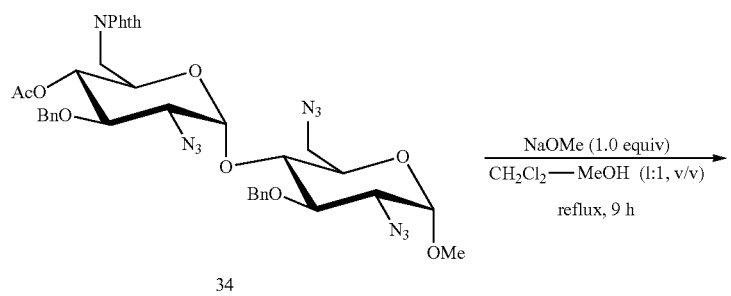
34

-continued
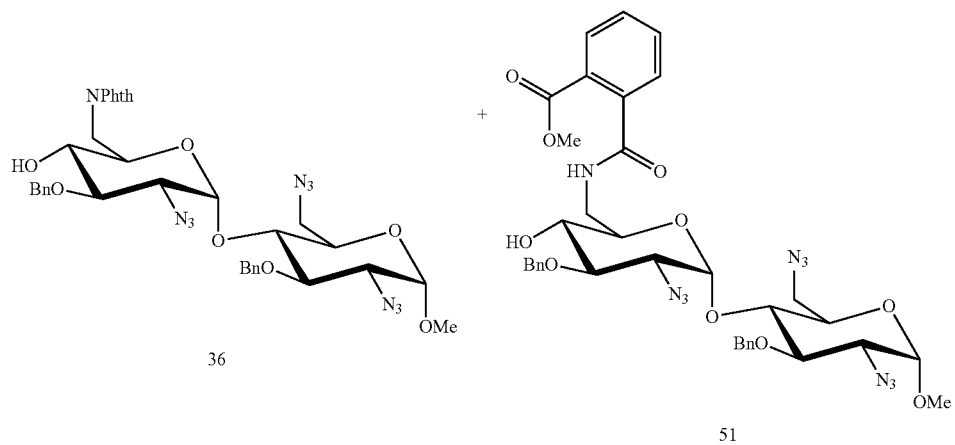
[Formula 11]
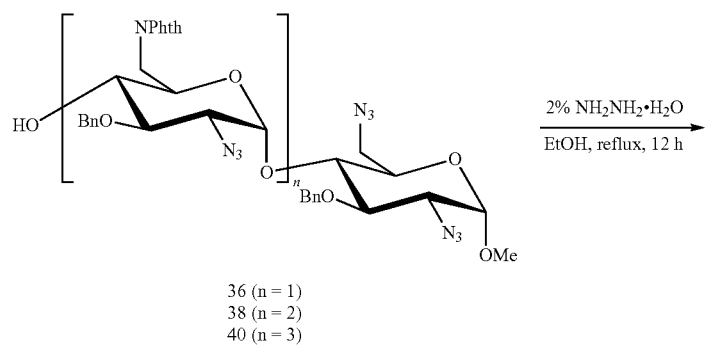
36 (n = 1)
38 (n = 2)
40 (n = 3)
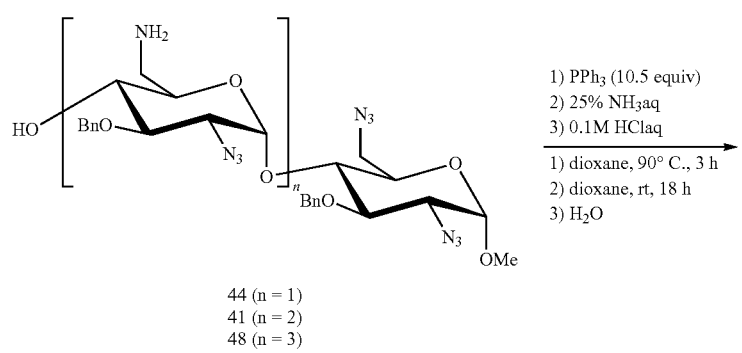
44 (n = 1)
41 (n = 2)
48 (n = 3)
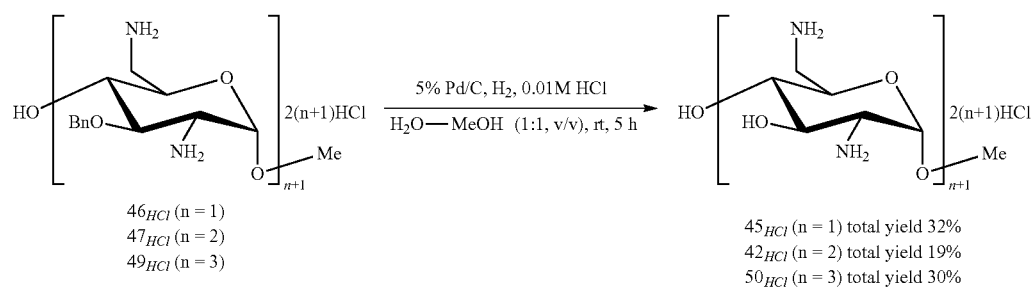
46$_{HCl}$ (n = 1)
47$_{HCl}$ (n = 2)
49$_{HCl}$ (n = 3)
45$_{HCl}$ (n = 1) total yield 32%
42$_{HCl}$ (n = 2) total yield 19%
50$_{HCl}$ (n = 3) total yield 30%

[Formula 12]

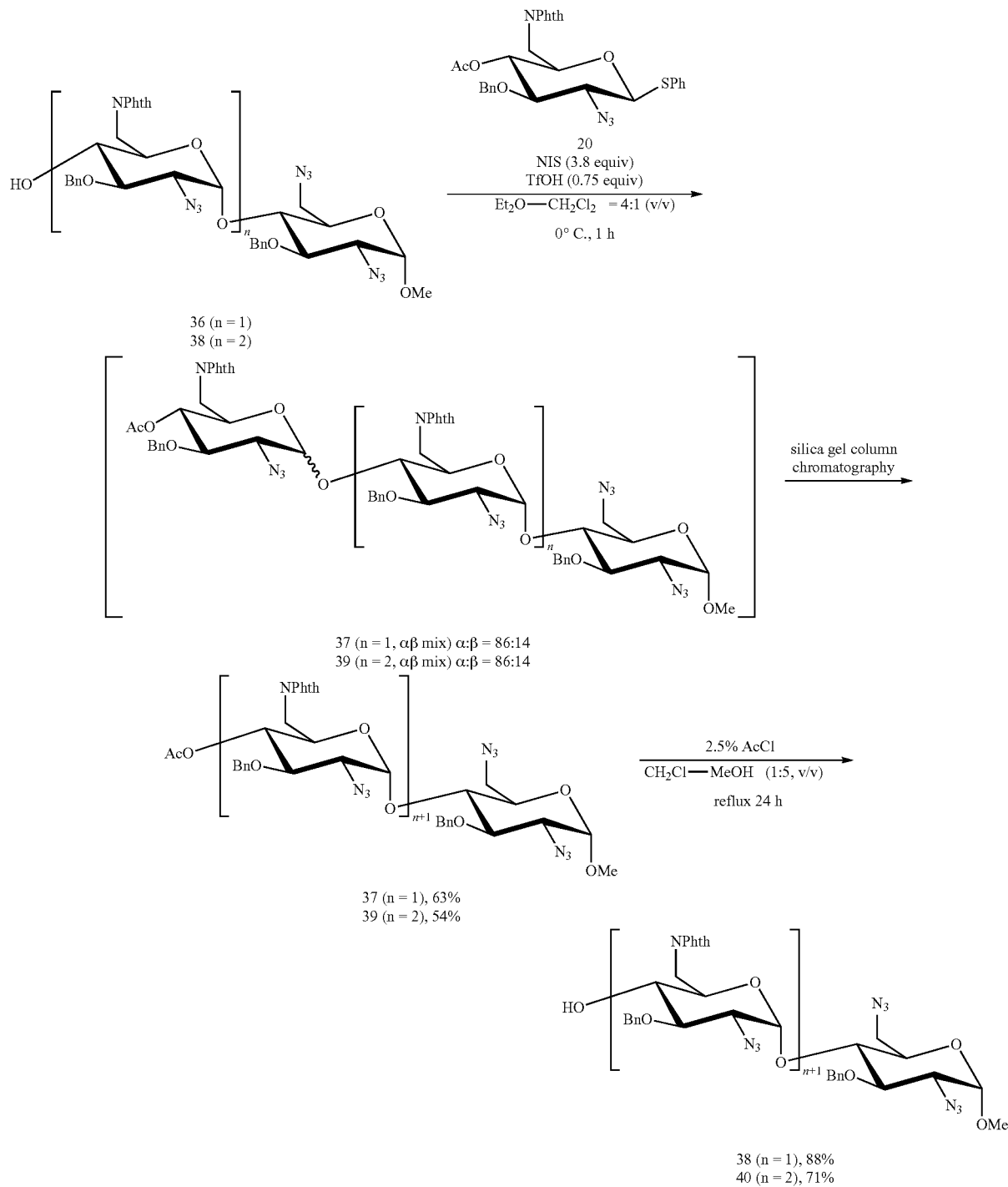

Method A: General Procedure for Glycosylation Reaction

Under an argon atmosphere, a glycosyl donor (100 μmol, 2.0 equiv) and a glycosyl acceptor (50 μmol) were azeotroped with toluene (1 ml) 6 times, and then added with N-iodosuccinimide (0.0562 g, 250 μmol, 5.0 equiv), and the mixture was dissolved in a mixed solvent of dichloromethane/diethyl ether (4:1, v/v, 1 ml). The mixture was cooled to 0° C. with stirring, and then added with trifluoromethanesulfonic acid (4.4 μlmul, 50 μmol, 1.0 equiv). The mixture was stirred for 1 hour, then added with water (2 μl), returned to room temperature by terminating the cooling, and added with 1 ml of saturated aqueous sodium hydrogencarbonate. The mixture was diluted with 10 ml of chloroform, transferred to a separating funnel, and washed once with each of 15 ml of saturated aqueous sodium hydrogencarbonate and 15 ml of 10% aqueous sodium thiosulfate. The organic layer was dried over anhydrous sodium sulfate, and the solvent was evaporated under reduced pressure. At this point, $^1$H-NMR measurement was performed to calculate the anomer ratio in the product. The product was purified by silica gel column chromatography to obtain an α-isomer of the glycosylation product.

Method B: Method for Determining Anomer Ratio in Glycosylation Product

H-1 of the α-isomer and H-2 of the β-isomer of 2-mer to 4-mer as the glycosylation product do not overlap with other signals in $^1$H-NMR spectrum of the mixture after the phase separation operation. Accordingly, the ratios were calculated from the ratios of integral values of the products.

Method C: Deacetylation with Acetyl Chloride

Under an argon atmosphere, a protected saccharide (36 μmol) was dissolved in dichloromethane (0.5 ml), and further added with methanol (2.5 ml). With stirring, the mixture was added with acetyl chloride (75 μl) and warmed, and the stirring was continued for 14 hours under reflux. After the mixture was gradually cooled to ordinary temperature, the mixture was added with saturated aqueous sodium hydrogencarbonate (1 ml), the solvent was evaporated under reduced pressure, then the residue was dissolved in chloroform (10 ml), and this solution was washed three times with saturated aqueous sodium hydrogencarbonate (10 ml). The organic layer was dried over anhydrous sodium sulfate, the solvent was evaporated, and then the residue was purified by silica gel column chromatography to obtain a deacetylated protected saccharide.

Method D: Elimination of Phthaloyl Group with Hydrazine and Reduction of Azido Group by Staudinger Reaction Under an argon atmosphere, a protected saccharide (14.6 μmol) was put into a egg-shaped flask, and successively added with ethanol (1 ml) and hydrazine monohydrate (25 μl). With stirring, the mixture was warmed, and left for 1 hour under reflux, and then stirring and heating were terminated. After the mixture was gradually cooled to ordinary temperature, the solvent was evaporated under reduced pressure, the residue was added with chloroform (2 ml), and the mixture was sonicated. The mixture was filtered, and extracted three times with chloroform/water in a separating funnel, the organic layer was dried over anhydrous sodium sulfate, and the solvent was evaporated under reduced pressure to obtain a mixture of the protected saccharide in which the phthalimido group was converted to amino group. The product was put into a 20-ml egg-shaped flask, and dissolved in a mixed solvent of dioxane/methanol (5:1, v/v, 1.8 ml). The mixture was added with triphenylphosphine (0.0714 g, 272 μmol, 6 equiv for 1 equiv of the azido group) with stirring under an argon atmosphere, and then refluxed by heating. After 3 hours, the mixture was cooled to ordinary temperature, and added with 25% aqueous ammonia (1.8 ml), and the mixture was sealed and stirred overnight. After the production of a sole single compound was monitored by TLC (iPrOH/25% NH$_3$ aq=9:2, v/v), the solvent was evaporated under reduced pressure, then the residue was successively added with water (4 ml) and 0.1 M aqueous hydrochloric acid (1 ml), and the mixture was sonicated for 1 minute. The mixture was filtered, the filtrate was washed three times with chloroform (10 ml) in a 30-ml separating funnel, and then the solvent was evaporated under reduced pressure. In order to completely remove hydrochloric acid, operations of adding water (3 ml) and evaporating the water under reduced pressure were further repeated three times, and thereby a benzyl-protected oligo-diaminosaccharide was obtained.

Method E: Reduction of Benzyl Group with Palladium

A protected saccharide (2.8 μmol) was put into a 20-ml two-neck egg-shaped flask, and added with 5% Pd/C (0.01 g). The mixture was added with a mixed solvent of water/methanol (1:1, v/v, 0.1 M HCl, 1.5 ml), and then hydrogen was added by bubbling. Disappearance of the spot of the starting material and formation of a single spot were confirmed by TLC (iPrOH-25% NH$_3$ aq (3:1, v/v)), the solvent was evaporated under reduced pressure, and operations of adding water (2 ml) and evaporating the water under reduced pressure were performed 4 times. The residue was dissolved in a very small volume of methanol (about 0.1 ml), and reprecipitated by adding the solution to acetone (3 ml). The mixture was centrifuged, the supernatant was removed, the residue was added with acetone, operations of centrifuging the mixture and removing the supernatant were repeated twice in a similar manner, and the obtained precipitates were dissolved in water and lyophilized to obtain an oligo-diaminosaccharide.

Phenyl 2-azido-2-deoxy-4,6-O-p-methoxybenzyliene-1-thio-β-D-glucopyranoside (10)

Under an argon atmosphere, 9 (2.81 g, 9.46 mmol) was azeotroped three times with acetonitrile (30 ml), and then dissolved in acetonitrile (200 ml). The solution was successively added with anisaldehyde dimethyl acetal (2.0 ml, 11.7 mmol, 1.24 equiv) and toluenesulfonic acid monohydrate (0.228 g, 0.98 mmol, 0.1 equiv) with stirring. After 1 hour, the mixture was further added with anisaldehyde dimethyl acetal (1.0 ml, 5.8 mmol, 0.62 equiv), and after further 1 hour, the mixture was added with triethylamine (1 ml). After the solvent was evaporated under reduced pressure, the residue was dissolved in ethyl acetate (100 ml), and washed three times with saturated aqueous sodium hydrogencarbonate (50 ml), the aqueous layer was back-extracted once with ethyl acetate (30 ml), and the organic layer was dried over anhydrous magnesium sulfate. After the solvent was evaporated under reduced pressure, the residue was crystallized by using a mixed solvent of ethyl acetate/hexane (1:9, v/v), and purified by silica gel column chromatography (ethyl acetate:hexane=1:1, v/v) to obtain 10 as colorless solid (3.33 g, 8.02 mmol, 85%).

$^1$H-NMR (CDCl$_3$) δ 7.52-7.57 (m, 2H, p-MeOPh), 7.33-7.38 (m, 5H, SPh), 6.86-6.89 (2H, p-MeOPh), 5.47 (s, 1H, benzylidene-CH), 4.53 (d, J=10.2, 1H, H-1), 4.35 (dd, J=10.7 and 3.9 Hz, 1H, H-6a), 3.72-3.79 (m, 5H, H-6b, H-3, OCH$_3$), 3.42-3.49 (m, 2H, H-4, H-5), 3.34 (t, J=9.9 Hz, 1H, H-2), 2.71 (d, J=2.8, 1H, 3-OH)

Phenyl 2-azido-2-deoxy-3-O-4,6-O-p-methoxybenzyliene-1-thio-β-D-glucopyranoside (11)

Under an argon atmosphere, 10 (3.33 g, 8.02 mmol) was azeotroped four times with pyridine and three times with toluene, and then dissolved in N,N-dimethylformamide (20 ml). Separately, under an argon atmosphere, sodium hydride (0.6512 g (60% purity), 16.0 mmol, 2.0 equiv) was added with hexane, the mixture was stirred, then the supernatant was discarded, and the residual hexane was evaporated. This procedure was repeated three times, and then the mixture was cooled to 0° C., and added with the solution of 10 in N,N-dimethylformamide. N,N-dimethylformamide used for washing of the vessel was also added to the mixture, and the total volume of the solvent became 80 ml. The mixture was added with benzyl bromide (1.45 ml, 12.0 mmol, 1.5 equiv) with stirring, and immediately warmed to ordinary temperature. After 1 hour, the mixture was added with methanol until bubbling ceased, and the solvent was evaporated under reduced pressure. The residue was added with dichloromethane (100 ml) and saturated aqueous sodium hydrogencarbonate (100 ml) to dissolve the whole system, then the aqueous layer was removed, and the organic layer was further washed twice with saturated aqueous sodium hydrogencarbonate (100 ml). The organic layer was dried over anhydrous sodium sulfate, then recrystallization was performed by using ethanol (1% triethylamine), and the crystals were collected up to secondary crystals to obtain 11 as colorless solid (3.73 g, 7.38 mmol, 92%).

$^1$H-NMR (CDCl$_3$) δ 7.50-7.55 (m, 2H, p-MeOPh), 7.28-7.39 (m, 10H, SPh, PhCH$_2$), 6.86-6.90 (m, 2H, p-MeOPh), 5.51 (s, 1H, benzylidene-CH), 4.89 (d, J=10.7, 1H, PhCH$_2$a), 4.75 (d, J=10.7 Hz, 1H, PhCH$_2$b), 4.47 (d, J=10.1 Hz, 1H, H-1), 4.35 (dd, J=5.0 and 10.5 Hz, 1H, H-6a), 3.72-3.79 (m, 4H, H-6b, OCH$_3$), 3.56-3.67 (m, 2H, H-4, H-3), 3.31-3.47 (m, 2H, H-2, H-5)

Phenyl 2-azido-2-deoxy-3-O-benzyl-4-O-p-methoxybenzyl-1-thio-β-D-glucopyranoside (12)

Under an argon atmosphere, 11 (0.121 g, 0.24 mmol) was azeotroped three times with pyridine and three times with toluene, and then dissolved in dichloromethane (1 ml). The solution was cooled to −20° C. with stirring, and added with 2.4 ml of a borane-THF complex (1 M solution in THF), and then the mixture was added with trimethylsilyl trifluoromethanesulfonate (25 μl, 0.14 mmol, 0.58 equiv). The mixture was stirred for 3.5 hours, and then further added with trimethylsilyl trifluoromethanesulfonate (25 μl, 0.14 mmol, 0.58 equiv). After 4 hours, the mixture was successively added with triethylamine (0.2 ml) and methanol (3 ml), and the solvent was evaporated. The residue was purified by silica gel column chromatography (dichloromethane:hexane:methanol=50:50:0→100:0:0→99:0:1→99:1:0, v/v/v) to obtain 12 as colorless solid (0.108 g, 0.21 mmol, 92%).

$^1$H-NMR (CDCl$_3$) δ 7.36-7.53 (m, 2H, p-MeOPh), 7.16-7.36 (m, 10H, SPh, PhCH$_2$), 6.83-6.86 (m, 2H, p-MeOPh), 4.86 (s, 2H, MeOPhCH$_2$), 4.74 (d, J=10.7 Hz, 1H, PhCH$_2$a), 4.55 (d, J=10.7 Hz, 1H, PhCH$_2$b), 4.43 (d, J=10.2 Hz, 1H, H-1), 3.84 (ddd, J=1.8, 6.3, and 12.1 Hz, 1H, H-6a), 3.66 (m, 1H, H-6b), 3.45-3.55 (m, 2H, H-3, H-4), 3.28-3.34 (m, 2H, H-2, H-5), 1.80 (dd, J=6.3 and 7.4 Hz, 1H, OH-6)

Phenyl 2-azido-2-deoxy-3-O-benzyl-4-O-p-methoxybenzyl-6-deoxy-5-phthalimido-1-thio-β-D-glucopyranoside (2)

Under an argon atmosphere, 12 (0.254 g, 0.5 mmol) was azeotroped three times with pyridine, and then dissolved in pyridine (5 ml). The solution was added with methanesulfonyl chloride (50 μl, 0.65 mmol, 1.3 equiv) at ordinary temperature with stirring. After 4 hours, the mixture was added with methanol (4 ml), the solvent was evaporated under reduced pressure, and the residue was dried by two times of azeotropy with toluene (3 ml), and then dissolved in dichloromethane. This solution was washed three times with saturated aqueous sodium hydrogencarbonate (20 ml), and the aqueous layer was back-extracted once with dichloromethane (10 ml). The collected organic layer was dried over anhydrous sodium sulfate. The solvent was evaporated under reduced pressure to obtain a mixture containing 13.

This mixture was azeotroped three times with N,N-dimethylformamide under an argon atmosphere, and then successively added with potassium phthalimide (0.119 g, 0.60 mmol, 1.2 equiv) and N,N-dimethylformamide (2.5 mL), the mixture was warmed with stirring, and stirring was continued at 100° C. for 15 hours. The heating was terminated, the mixture was gradually cooled to ordinary temperature, then the solvent was evaporated under reduced pressure, and the residue was added with dichloromethane and 10% aqueous sodium chloride to dissolve the whole residue. The aqueous layer was removed by phase separation, the organic layer was washed three times with 10% aqueous sodium chloride, and the aqueous layer was back-extracted with dichloromethane. The organic layer was dried over anhydrous sodium sulfate, and filtered, and then the solvent was evaporated. The residue was purified by silica gel column chromatography (dichloromethane:hexane=7:3→10:0, v/v) and then crystallized from hexane to obtain 2 as colorless crystals (0.149 g, 0.235 mmol, 47%).

$^1$H-NMR (CDCl$_3$) δ 7.70-7.83 (m, 4H, NPhth), 6.82-7.35 (m, 14H, p-MeOPh, PhCH2, SPh), 4.81-4.90 (m, 3H, MeOPhCH$_2$, PhCH$_2$a), 4.65 (d, J=10.7 Hz, 1H, PhCH$_2$b), 4.27 (d, J=9.9 Hz, 1H, H-1), 3.90 (dd, J=3.3 and 14.0 Hz, 1H, H-6a), 3.74-3.82 (m, 4H, H-6b, OCH$_3$), 3.66 (dt, J=3.3 (d) and 8.8 (t) Hz, 1H, H-5), 3.50 (t, J=9.0 Hz, 1H, H-3), 3.26-3.38 (m, 2H, H-2, H-4)

Phenyl 2-azido-2-deoxy-3-O-benzyl-6-deoxy-6-phthalimido-1-thio-β-D-glucopyranoside (19)

Under an argon atmosphere, 17 (5.417 g, 14.0 mmol) was dried by three times of azeotropy with pyridine (10 mL), and dissolved in pyridine (200 ml). The solution was added with methanesulfonyl chloride (1.1 ml, 14.3 mmol, 1.02 equiv) at −15° C. with stirring. The reaction system was stirred for 5 hours, and then added with methanol (10 ml), and the solvent was evaporated under reduced pressure. The residue was dried by two times of azeotropy with toluene (10 mL), and dissolved in chloroform (100 mL). This solution was washed three times with saturated aqueous sodium hydrogencarbonate (100 mL), added with anhydrous sodium sulfate and dried. The solvent was evaporated under reduced pressure to obtain a mixture containing 18.

This mixture was subjected to azeotropy three times with N,N-dimethylformamide (15 mL) under an argon atmosphere, and successively added with potassium phthalimide (4.89 g, 26.4 mmol) and N,N-dimethylformamide (140 mL), the mixture was warmed with stirring, and stirring was continued at 100° C. for 13 hours. After heating was terminated, the mixture was gradually cooled to ordinary temperature, then the solvent was evaporated under reduced pressure, and the residue was added with chloroform and 10% aqueous sodium chloride to dissolve the whole residue. The aqueous layer was removed by phase separation, and the organic layer was washed twice with 10% aqueous sodium chloride (100 mL). The organic layer was dried over anhydrous sodium sulfate and filtered, and then the solvent was evaporated. The residue was recrystallized from ethanol (400 mL), and crystals were collected up to secondary crystals to obtain 19 as colorless crystals (5.28 g, 10.2 mmol, 73%).

$^1$H-NMR (CDCl$_3$) δ 7.74-7.88 (m, 4H, NPhth), 7.02-7.51 (m, 10H, SPh, Ph-CH$_2$), 4.81-4.86 (dd, J=10.7 and 16.5 Hz, 2H, Ph-CH$_2$), 4.32 (d, J=10.2 Hz, 1H, H-1), 4.16 (dd, J=3.3 and 14.6 Hz, 1H, H-6a), 3.97 (dd, J=4.1 and 14.6 Hz, 1H, H-6b), 3.48-3.54 (m, 1H, 5-H), 3.38 (t, J=9.0 Hz, 1H, 3-H), 3.25 (m, 1H, 4H), 3.10 (dd, J=9.1 and 10.2 Hz, 1H, 2H)

Phenyl 4-acetyl-2-azido-2-deoxy-3-O-benzyl-6-deoxy-6-phthalimido-1-thio-β-D-glucopyranoside (20)

Under an argon atmosphere, 19 (5.28 g, 10.2 mmol) was dissolved in pyridine (100 ml), and the solution was added with acetic anhydride (1.5 ml, 1.59 mmol, 1.56 equiv) with stirring. After three days, stirring was terminated, and the solvent was evaporated. The residue was dissolved in chloroform, and the solution was washed three times with saturated aqueous sodium hydrogencarbonate in a separating funnel. The organic layer was dried over anhydrous sodium sulfate, then recrystallization was performed by using ethanol (50 ml), and primary crystals were collected to obtain 20 as colorless solid (5.29 g, 9.5 mmol, 93%).

$^1$H-NMR (CDCl$_3$) δ 7.72-7.86 (m, 4H, NPhth), 6.98-7.42 (m, 10H, SPh, Ph-CH$_2$), 4.79-4.90 (m, 2H, H-4, Ph-CH$_2$a), 4.63 (d, J=11.3 Hz, 1H, Ph-CH$_2$b), 4.36 (d, J=9.9 Hz, 1H, H-1), 4.00 (dd, J=9.6 and 14.0 Hz, 1H, H-6a), 3.72 (dt, J=2.5 (d) and 9.6 (t) Hz, 1H, H-5), 3.57 (dd, J=2.5 and 14.0 Hz, 1H, H-6b), 3.49 (t, J=9.3 Hz, 1H, 3-H), 3.35 (t, J=9.3 Hz, 1H, H-2), 2.00 (s, 3H, Ac)

Phenyl 4-acetyl-2,6-diazido-2,6-dideoxy-3-O-benzyl-1-thio-β-D-glucopyranoside (22)

Under an argon atmosphere, 17 (0.194 g, 0.5 mmol) was dried by three times of azeotropy with pyridine, and dissolved in pyridine (10 ml). The solution was added with methanesulfonyl chloride (43 μl, 0.53 mmol, 1.06 equiv) at −15° C. with stirring. The reaction system was stirred for 11 hours, and then added with methanol (2 ml), and the solvent was evaporated under reduced pressure. The residue was dried by two times of azeotropy with toluene (7 mL), and then dissolved in chloroform. This solution was washed three times with saturated aqueous sodium hydrogencarbonate (15 mL), added with anhydrous sodium sulfate and dried. The solvent was evaporated under reduced pressure to obtain a mixture containing 18.

This mixture was subjected three times to azeotropy using N,N-dimethylformamide (8 mL) under an argon atmosphere, and successively added with sodium azide (0.324 g, 5.0 mmol, 10 equiv) and N,N-dimethylformamide (5 mL), the mixture was warmed with stirring, and stirring was continued at 80° C. for 12 hours. After heating was terminated, the mixture was gradually cooled to ordinary temperature, then the solvent was evaporated under reduced pressure, and the residue was extracted once with ethyl acetate/water (10 ml). Then, the organic layer was washed twice with water (10 ml), and all the aqueous layers were collected and back-extracted once with ethyl acetate (20 ml). The organic layer was dried over anhydrous magnesium sulfate, and the solvent was evaporated to obtain a mixture containing 21.

This mixture was dissolved in pyridine (5 ml) under an argon atmosphere, and the solution was added with acetic anhydride (75 μl, 0.79 mmol, 1.58 equiv) with stirring. After 28 hours, stirring was terminated, and the solvent was evaporated. The residue was dissolved in chloroform, and the solution was washed twice with saturated aqueous sodium hydrogencarbonate in a separating funnel. The organic layer was dried over anhydrous sodium sulfate, the solvent was evaporated, and the residue was purified by silica gel column chromatography (chloroform) to obtain 22 as colorless oil (0.196 g, 0.43 mmol, 86%).

$^1$H-NMR (CDCl$_3$) δ 7.28-7.62 (m, 10H, SPh, Ph-CH$_2$), 4.80-4.90 (m, 2H, H-4, Ph-CH$_2$a), 4.62 (d, J=11.3 Hz, 1H, Ph-CH$_2$b), 4.43 (d, J=9.9 Hz, 1H, H-1), 3.47-3.54 (m, 2H, H-3, H-5), 3.22-3.39 (m, 3H, H-2, H-6), 1.96 (s, 3H, Ac)

Methyl O-(2,6-diazido-2,6-dideoxy-3-O-benzyl-α-D-glucopyranoside) (4)

Under an argon atmosphere, 32 (2.00 g, 6.40 mmol) was azeotroped three times with pyridine (15 ml), and then dissolved in pyridine (130 ml). The solution was cooled to −15° C., and added with methanesulfonyl chloride (0.50 ml, 6.46 mmol, 1.02 equiv), and the mixture was stirred for 7 hours and then successively added with methanol (5 ml) and saturated aqueous sodium hydrogencarbonate (3 ml). The solvent was evaporated under reduced pressure, and the residue was dissolved in ethyl acetate (100 ml). This solution was washed this three times with saturated aqueous sodium hydrogencarbonate (50 ml), and the aqueous layer was back-extracted once with ethyl acetate (50 ml). The organic layer was dried over anhydrous magnesium sulfate, and the solvent was evaporated under reduced pressure to obtain a mixture of 33.

This mixture was azeotroped three times with N,N-dimethylformamide (10 mL) under an argon atmosphere, and then dissolved in N,N-dimethylformamide (64 ml), the solution was added with sodium azide (4.16 g, 64 mmol, 10 equiv), and the mixture was warmed to 80° C. with stirring. After 10.5 hours, the mixture was gradually cooled to ordinary temperature, the solvent was evaporated under reduced pressure, and then the residue was dissolved in ethyl acetate (100 ml). This solution was washed three times with water (50 ml), and the aqueous layer was back-extracted once with ethyl acetate (50 ml). The organic layer was dried over anhydrous magnesium sulfate, and the solvent was evaporated under reduced pressure. The residue was purified by silica gel column chromatography (dichloromethane:hexane=2:1→1:0, v/v) to obtain 4 as pale yellow oil (1.76 g, 5.3 mmol, 82%).

$^1$H-NMR (CDCl$_3$) δ 7.31-7.43 (m, 5H, Ph-CH$_2$), 4.99 (d, J=11.2 Hz, 1H, Ph-CH$_2$a), 4.83 (d, J=3.6 Hz, 1H, H-1), 4.67 (d, J=11.6 Hz, 1H, Ph-CH$_2$b), 3.73-3.80 (m, 2H, H-3, H-5 or H-6), 3.36-3.55 (m, 6H, H-4, OCH$_3$, H-5 or H-6), 2.08 (d, J=2.8 Hz, 1H, OH-4), 3.35 (t, 1H, H-2)

Methyl O-(2,6-diamino-2,6-dideoxy-α-D-glucopyranoside)hydrochloride (43)

43 was obtained as colorless solid (19.1 μmol, 80%) by Method E using 4 (8.0 mg, 24 μmol) as the starting material.

$^1$H-NMR (D$_2$O) δ 5.07 (d, J=3.9 Hz, 1H, H-1), 3.86-3.90 (m, 2H, H-3, H-5), 3.22-3.51 (m, 6H, H-2, H-4, OCH$_3$, H-6a), 3.17 (dd, J=10.4 and 13.5 Hz, 1H, H-6b)

MALDI-TOF MS: calcd for C$_7$H$_{16}$N$_2$O$_4$ m/z [M+Na]$^+$: 215.10 Found: 215.30

Methyl O-((4-O-acetyl-2-azido-2-deoxy-3-O-benzyl-6-deoxy-6-phthalimido-α-D-glucopyranosyl)-(1→4)-2,6-d-azido-2,6-dideoxy-3-O-benzyl-α-D-glucopyranoside) (34)

Method A was used with 20 (100 μmol, 56.1 mg) and 4 (50 μmol) as the starting materials. Ethyl acetate/hexane (3:7) was used as the developing solvent in silica gel column chromatography to obtain 34 as pale yellow oil (20.4 mg, 26 μmol, 63%).

$^1$H-NMR (CDCl$_3$) δ 7.72-7.88 (m, 4H, NPhth), 7.28-7.38 (m, 10H, Ph-CH$_2$), 5.61 (d, J=3.9 Hz, 1H, H-1'), 4.95 (m, 2H, H-4', Ph-CH$_2$a), 4.80-4.86 (m, 2H, Ph-CH$_2$b, Ph-CH$_2$c), 4.74 (d, J=3.3 Hz, 1H, H-1), 4.65 (d, J=11.0 Hz, 1H, Ph-CH$_2$d), 3.89-4.00 (m, 4H, H-3', H-6a', H-6b', H-3), 3.75 (m, 1H, H-5), 3.60-3.66 (m, 2H, H-5', H-4), 3.27-3.39 (m, 6H, H-2, H-6a, H-2', OCH$_3$), 3.01 (dd, J=4.4 and 13.2 Hz, 1H, H-6b), 2.05 (s, 3H, Ac)

Methyl O-(2-azido-2-deoxy-3-O-6-phthalimido-6-deoxy-α-D-glucopyranosyl)-(1→4)-2,6-d-azido-2,6-dideoxy-3-O-benzyl-α-D-glucopyranoside) (36)

Method C was used with 34 (0.148 g, 0.19 mmol) as the starting material, and ethyl acetate/toluene (1:9, v/v) was used as the developing solvent in silica gel column chromatography to obtain 36 as pale yellow oil (0.123 g, 0.165 mmol, 88%).

$^1$H-NMR (CDCl$_3$) δ 7.72-7.88 (m, 4H, NPhth), 7.24-7.42 (m, 10H, Ph-CH$_2$), 5.51 (d, J=3.9 Hz, 1H, H-1'), 4.83-4.97 (m, 5H, H-1, Ph-CH$_2$), 4.10 (dd, J=3.3 and 14.6 Hz, 1H, H-6a'), 3.85-4.04 (m, 4H, H-3', H-5', H-6', H-3), 3.71-3.78 (m, 2H, H-3, H-5), 3.35-3.56 (m, 8H, H-4', H-6b, H-2, OCH$_3$, H-6a, OH-4'), 3.21 (dd, J=4.1 and 10.2 Hz, 1H, H-2)

Methyl O-((2,6-diamino-2,6-dideoxy-3-O-benzyl-α-D-glucopyranosyl)-(1→4)-2,6-diamino-2,6-dideoxy-3-O-benzyl-α-D-glucopyranoside)hydrochloride (46)

Method D was used with 36 (10.8 mg, 14.6 μmol) as the starting material to obtain 46 as colorless oil (12.3 μmol, 84%).

$^1$H-NMR (D$_2$O) δ 7.38-7.45 (m, 10H, Ph-CH$_2$), 5.64 (d, J=3.3 Hz, 1H, H-1'), 5.14 (d, J=3.9 Hz, 1H, H-1), 4.68-4.89 (m, 4H, Ph-CH$_2$), 4.38 (dd, J=8.0 and 10.5 Hz, 1H), 4.13-4.19 (m, 2H), 3.78-3.94 (m, 3H), 3.70 (t, J=8.0 Hz, 1H), 3.31-3.56 (m, 8H)

Methyl O-((2,6-diamino-2,6-dideoxy-α-D-glucopyranosyl)-(1→4)-2,6-dideoxy-α-D-glucopyranoside hydrochloride (45)

Method E was used with 46 (5.2 μmol) as the starting material to obtain 45 as colorless solid (2.0 μmol, 38%).

$^1$H-NMR (D$_2$O) δ 5.78 (d, J=3.3 Hz, 1H, H-1'), 5.09 (d, J=3.6 Hz, 1H, H-1), 4.03-4.18 (m, 2H, H-5, H-3), 3.76-3.88 (m, 3H, H-4, H-5', H-3'), 3.38-3.53 (m, 8H, H-2', H-6a, H-6a', H-2, OCH$_3$, H-4'), 3.24-3.48 (m, 2H, H-6b, H-6b')

MALDI-TOF MS: calcd for C$_{13}$H$^{28}$N$_4$O$_7$ m/z [M+Na]$^+$: 375.19 Found: 375.79

Methyl O-((4-O-acetyl-2-azido-2-deoxy-3-O-benzyl-6-deoxy-6-phthalimido-α-D-glucopyranosyl)-(1→4)-(2-azido-2-deoxy-3-O-benzyl-6-deoxy-6-phthalimido-α-D-glucopyranosyl)-(1→4)-2,6-diazido-2,6-dideoxy-3-O-benzyl-α-D-glucopyranoside) (37)

Method A was used with 20 (0.209 mmol, 0.117 g) and 36 (0.139 mmol, 0.103 g) as the starting materials. As for silica gel column chromatography, toluene/ethyl acetate (9:1) and ethyl acetate hexane (7:13) were used in this order as the developing solvent to obtain 37 as colorless oil (0.105 g, 88 μmol, 63%).

$^1$H-NMR (CDCl$_3$) δ 7.57-7.90 (m, 8H, NPhth), 7.31-7.57 (m, 15H, Ph-CH$_2$), 5.59 (d, J=3.9 Hz, 1H, H-1"), 5.49 (d, J=3.6 Hz, 1H, H-1'), 4.71-5.05 (m, 8H, H-1, Ph-CH$_2$, H-4"), 4.34 (t, J=8.7 Hz, 1H, H-5"), 4.09-4.17 (m, 3H), 3.87-3.98 (m, 3H), 3.54-3.75 (m, 5H), 3.23-3.43 (m, 8H), 3.14 (dd, J=3.6 and 10.2 Hz, 1H, H-2'), 2.98 (dd, J=4.1 and 13.5 Hz, 1H), 2.07 (s, 3H, Ac)

Methyl O-((2-amino-2-deoxy-3-O-benzyl-6-deoxy-6-phthalimido-α-D-glucopyranosyl)-(1→4)-(2-amino-2-deoxy-3-O-benzyl-6-deoxy-6-phthalimido-α-D-glucopyranosyl)-(1→4)-2,6-d-azido-2,6-dideoxy-3-O-benzyl-α-D-glucopyranoside) (38)

Method C was used with 37 (81.8 mg, 69 μmol) as the starting material. As the developing solvent for silica gel column chromatography, ethyl acetate/toluene (3:17, v/v) was used to obtain 38 as colorless oil (69.2 mg, 60 μmol, 88%).

$^1$H-NMR (CDCl$_3$) δ 7.65-7.91 (m, 8H, NPhth), 7.29-7.46 (m, 15H, Ph-CH$_2$), 5.57 (d, J=3.3 Hz, 1H, H-1' or H-1"), 5.47 (d, J=4.1 Hz, 1H, H-1' or H-1"), 4.79-5.07 (m, 6H, Ph-CH$_2$,), 4.80 (d, J=10.2 Hz, 1H, H-1), 4.27 (m, 1H), 3.91-4.09 (m, 6H), 3.35-3.84 (m, 14H), 3.03 (J=3.9 and 10.5 Hz, dd, 1H, H-2' or H-2")

Methyl O-((2,6-diamino-2,6-dideoxy-3-O-benzyl-α-D-glucopyranosyl)-(1→4)-(2,6-diamino-2,6-dideoxy-3-O-benzyl-α-D-glucopyranosyl)-(1→4)-2,6-diamino-2,6-dideoxy-3-O-benzyl-α-D-glucopyranoside)hydrochloride (47)

Method D was used with 38 (9.8 mg, 8.5 μmol) as the starting material, and then the resultant was purified by reverse phase HPLC. The solvent was evaporated under reduced pressure, the residue was added with 0.1 M hydrochloric acid (1 ml), the mixture was sonicated, the solvent was evaporated, and then operations of adding water and evaporating the water was performed twice to obtain 47 as colorless oil (2.80 μmol, 33%). The reverse phase HPLC was performed with a water-acetonitrile system (0.05% TFA), water:acetonitrile=100:0→65:35 was used for 0 to 70 minutes, and water:acetonitrile=65:35→50:50 was used for 70 to 85 minutes, and the peak at 60.06 minutes was collected.

$^1$H-NMR (D$_2$O) δ 7.20-7.42 (m, 15H, Ph-CH$_2$), 5.48 (d, J=1.9 Hz, 1H, H-1' or H-1"), 5.35 (d, J=3.6 Hz, 1H, H-1' or H-1"), 5.10 (d, J=3.6 Hz, 1H, H-1), 4.71-4.99 (6H, Ph-CH$_2$), 4.51-4.57 (m, 3H), 4.07-4.28 (m, 6H), 3.80-3.88 (m, 1H), 3.74 (t, J=8.5 Hz, 1H), 3.36-3.60 (m, 10H), 3.15-3.22 (m, 2H)

Methyl O-((2,6-diamino-2,6-dideoxy-α-D-glucopyranosyl)-(1→4)-(2,6-diamino-2,6-dideoxy-α-D-glucopyranosyl)-(1→4)-2,6-diamino-2,6-dideoxy-α-D-glucopyranoside)hydrochloride (42)

Method E was used with 47 (2.80 μmol) as the starting material to obtain 42 (1.37 μmol, 49%) as colorless solid.

$^1$H-NMR (D$_2$O) δ 5.78-5.83 (2d, J=3.9 Hz, 3.9 Hz, 2H, H-1', H-1"), 5.10 (d, J=3.6 Hz, 1H, H-1), 4.03-4.24 (m, 4H), 3.80-3.94 (m, 4H), 3.28-3.55 (m, 13H)

MALDI-TOF MS: calcd for C$_{15}$H$_{40}$N$_6$O$_{10}$ m/z [M+Na]$^+$: 535.27 Found: 536.02

Methyl O-((4-O-acetyl-2-diazido-2-dideoxy-3-O-benzyl-6-deoxy-6-phthalimido-α-D-glucopyranosyl)-(1→4)-(2-diazido-2-dideoxy-3-O-benzyl-6-deoxy-6-phthalimido-α-D-glucopyranosyl)-(1→4)-2-diazido-2-dideoxy-3-O-benzyl-6-deoxy-6-phthalimido-α-D-glucopyranosyl-(1→4)-2,6-d-azido-2,6-dideoxy-3-O-benzyl-α-D-glucopyranoside) (39)

Method A was used with 20 (0.209 mmol, 0.117 g) and 38 (0.139 mmol, 0.103 g) as the starting materials. As the developing solvent for silica gel column chromatography, toluene/ethyl acetate (9:1) and ethyl acetate/hexane (7:13) were used in this order to obtain 39 as colorless oil (0.105 g, 88 μmol, 63%).

$^1$H-NMR (CDCl$_3$) δ 7.59-7.88 (m, 12H, NPhth), 7.30-7.36 (m, 20H, Ph-CH$_2$), 5.55 (d, J=3.9 Hz, 1H, H-1' or H-1"), 5.44-5.48 (2d, 3.6 Hz, 3.9 Hz, 2H, H-1' or H-1'"), 4.73-5.03 (m, 10H, H-1, Ph-CH$_2$, H-4"), 4.08-5.03 (m, 4H), 3.71-3.96

(m, 7H), 3.15-3.98 (m, 13H), 3.09 (dd, J=3.6 and 10.3 Hz, 1H, H-2' or H-2"), 3.00 (dd, J=4.4 and 13.5 Hz, 1H), 1.97 (s, 3H, Ac)

Methyl O-(2-azido-2-deoxy-3-O-benzyl-6-deoxy-6-phthalimido-α-D-glucopyranosyl)-(1→4)-(2-azido-2-deoxy-3-O-benzyl-6-deoxy-6-phthalimido-α-D-glucopyranosyl)-(1→4)-(2-azido-2-deoxy-3-O-benzyl-6-deoxy-6-phthalimido-α-D-glucopyranosyl)-(1→4)-(2,6-d-azido-2,6-dideoxy-3-O-benzyl-α-D-glucopyranoside (40)

Method C was used with 39 (53.3 mg, 33 μmol) as the starting material. As the developing solvent for silica gel column chromatography, ethyl acetate/toluene (1:6, v/v) was used to obtain 40 as colorless oil (36.6 mg, 23.6 μmol, 71%).

$^1$H-NMR (CDCl$_3$) δ 7.64-7.91 (m, 12H, NPhth), 7.31-7.42 (m, 20H, Ph-CH$_2$), 5.33-5.53 (3d, J=3.9 Hz, J=3.6 Hz, J=3.9 Hz, 3H, H-1', H-1", H-1'''), 4.72-5.14 (m, 9H, H-1, Ph-CH$_2$), 4.43 (t, 1H), 4.11-4.29 (m, 4H), 3.54-4.04 (m, 11H), 3.26-3.46 (m, 10H), 3.11 (dd, J=1H, J=3.6 and 10.2 Hz, H-2' or H-2" or H-2'''), 3.01 (dd, J=3.9 and 13.5 Hz, 1H)

Methyl O-((2,6-diamino-2,6-dideoxy-3-O-benzyl-α-D-glucopyranosyl)-(1→4)-(2,6-diamino-2,6-dideoxy-3-O-benzyl-α-D-glucopyranosyl)-(1→4)-(2,6-diamino-2,6-dideoxy-3-O-benzyl-α-D-glucopyranosyl)-(1→4)-2,6-diamino-2,6-dideoxy-3-O-benzyl-α-D-glucopyranoside)hydrochloride (49)

Method D was used with 40 (13.7 mg, 8.8 μmol) as the starting material, and then the resultant was purified by reverse phase HPLC. The solvent was evaporated under reduced pressure, then the residue was added with 5 ml of 0.02 M hydrochloric acid, the mixture was sonicated, and the solvent was evaporated. Then, operations of adding water and evaporating the water were repeated four times to obtain 49 as colorless oil (2.82 μmol, 32%). The reverse phase HPLC was performed with a water-acetonitrile system (0.05% TFA), water:acetonitrile=100:0→75:25 was used for 0 to 25 minutes, water:acetonitrile=75:25→65:35 was used for 25 to 65 minutes, then water:acetonitrile=65:35→50:50 was used, and the peak at 40.96 minutes was collected.

$^1$H-NMR (D$_2$O) δ 7.31-7.46 (m, 20H, Ph-CH$_2$), 5.46-5.62 (3d, J=2.8 Hz, J=3.0 Hz, J=2.5 Hz, 3H, H-1', H-1", H-1'''), 5.16 (d, J=3.9 Hz, 1H, H-1), 4.69-4.94 (8H, Ph-CH$_2$), 4.33-4.49 (m, 4H), 4.02-4.26 (m, 7H), 3.67-3.80 (m, 4H), 3.32-3.57 (m, 2H)

Methyl O-((2,6-diamino-2,6-dideoxy-α-D-glucopyranosyl)-(1→4)-(2,6-diamino-2,6-dideoxy-α-D-glucopyranosyl)-(1→4)-(2,6-diamino-2,6-dideoxy-α-D-glucopyranosyl)-(1→4)-(2,6-diamino-2,6-dideoxy-α-D-glucopyranoside)hydrochloride (50)

Method E was used with 49 (2.82 μmol) as the starting material to obtain 50 as colorless solid (2.59 μmol, 93%).

$^1$H-NMR (D$_2$O) δ 5.81-5.87 (m, 3H, H-1', H-1", H-1'''), 5.11 (d, J=3.6 Hz, 1H, H-1), 4.10-4.34 (m, 6H), 3.82-3.96 (m, 5H), 3.31-3.60 (m, 16H)

MALDI-TOF MS: calcd for $C_{25}H_{52}N_8O_{13}$ m/z [M+Na]+: 695.36 Found: 695.80

Example 2

Interactions of the oligo-diaminosaccharides obtained in Example 1 (monosaccharide: 43, disaccharide: 45, trisaccharide: 42, tetrasaccharide: 50) with double-stranded nucleic acids were spectrophotometrically analyzed. As the analysis methods, CD spectrum analysis and UV melting point analysis were selected. As for the CD spectrum analysis, information on structural change of double strand can be obtained from change of the spectrum, and as for the UV melting point (Tm) analysis, information on stability of double strand can be obtained from the melting point, and information on stacking degree of bases of nucleic acid can be obtained from the hypochromic effect.

Several types of double helix structures of nucleic acids are known. It is also known that DNA, most of which molecules exist in the form of double helix in vivo, has the B-type helical structure under a physiological condition. Further, it is known that RNA double strands have the A-type double helix structure, which has a major groove narrower than that of the B-type double helix structure. Interactions of the compounds of the present invention with each of RNA double strands having the A-type helical structure and double strands DNA having the B-type helical structure were analyzed. The following experiments were performed in a 100 mM sodium chloride and 10 mM phosphate buffer, pH 6.91, unless specifically indicated, and all the CD spectra were measured at 25° C. All the oligo-diaminosaccharides were used as hydrochlorides.

The experiments were performed by using two kinds of self-complementary 12-mers, r(CGCGAAUUCGCG)$_2$ (SEQ ID NO: 6) (hereinafter referred to as "I") and r(AAC-CCGCGGGUU)$_2$ (SEQ ID NO: 7) (hereinafter referred to as "II") as target RNAs. These nucleic acids are self-complementary RNAs, and accordingly, experimental procedure can be simplified, and as they contain two or more of each kind of base, they have little ununiformity of the base composition. I and II have the same base composition and are different only in the sequences.

In the case of a 12-mer double-stranded nucleic acid, the nucleic acid contains 11 pairs of phosphate moieties, i.e., 22 phosphate moieties, per one double helix. Therefore, for complete binding of all the phosphate moieties with the amino groups, 11 equivalents (equivalents to the double-stranded nucleic acid) of the monosaccharide 43, 6 equivalents of the disaccharide 45, 4 equivalents of the trisaccharide 42, or 3 equivalents of the tetrasaccharide 50 is required. It was necessary to use the same equivalents of the amino group of the saccharides, especially for the comparison of Tm. For that purpose, the saccharides were used in the numbers of equivalent mentioned above as the standards, except that the monosaccharide 43 was used in an amount of 12 equivalents.

For comparison, similar measurements were performed for neomycin and tobramycin, which are amino-containing saccharide compounds already known to interact with nucleic acids. Since neomycin has 6 amino groups, and tobramycin has 5 amino groups, it is necessary to perform the comparison either by using "the same equivalents as the molecules" or "the same equivalents of amino groups". Both of the comparisons can be performed for neomycin, whist no comparison can be performed with the same equivalents of amino groups because tobramycin has 5 amino groups. Therefore, for tobramycin, the comparison was performed with the same equivalents as the molecules.

[Formula 13]

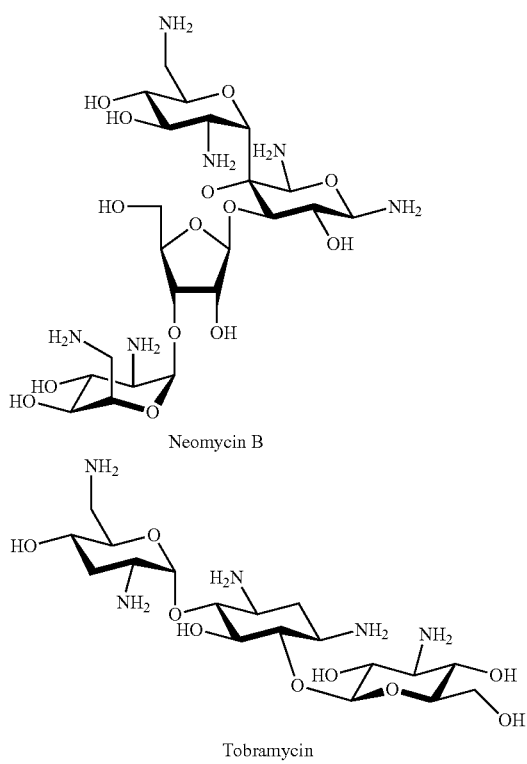

Neomycin B

Tobramycin

The CD spectrum of I is characterized by the large positive peak induced by the Cotton effect at around 265 nm, which is unique to the A-type double helix structure. As shown in FIGS. 1, (A) and (B), the intensity was increased by 8%, 14%, 9% and 24% in the systems added with the monosaccharide 43, the disaccharide 45, the trisaccharide 42, and the tetrasaccharide 50, respectively, and in particular, in the systems added with the trisaccharide 42 and the tetrasaccharide 50, the peaks shifted by about 2 nm to the longer wavelength side. This result indicates that structural change of the RNA double strands was induced by the addition of the oligo-diaminosaccharides. Then, changes caused by different equivalents of the tetrasaccharide 50 were observed, and the result shown in FIG. 1(C) was obtained. The peak intensity was already increased by 17% when 1 equivalent of the tetrasaccharide was added, and the increase became relatively small thereafter. Whist the peak was shifted by 1 nm when 1 equivalent of the tetrasaccharide was added, and by 1.6 nm when 2 equivalents of the tetrasaccharide was added, indicating that the peak was still shifted even when 2 equivalents of the tetrasaccharide was added.

Figure 2:
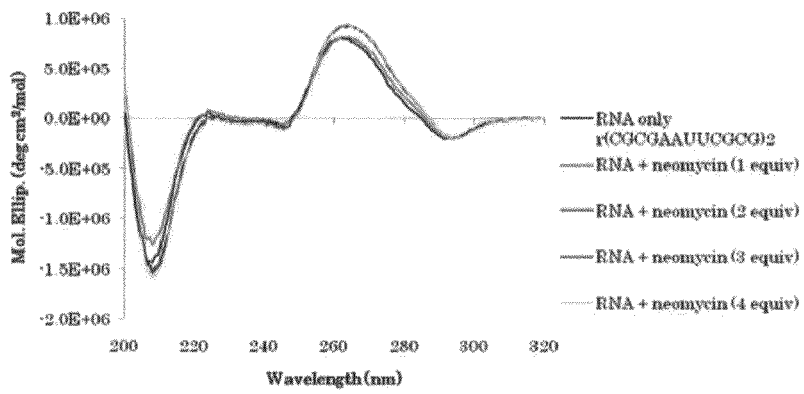
FIG. 2 depicts CD spectra of RNA (I) (SEQ ID NO: 6).

For comparison, similar measurements were performed for neomycin (FIG. 2). Also in this case, the positive peak at around 265 nm slightly shifted to the long wavelength side, and thus the same change as that observed for the systems added with the trisaccharide 42 and the tetrasaccharide 50 was observed. This result suggests that a structural change similar to that induced by the oligo-diaminosaccharides was induced.

Figure 3:
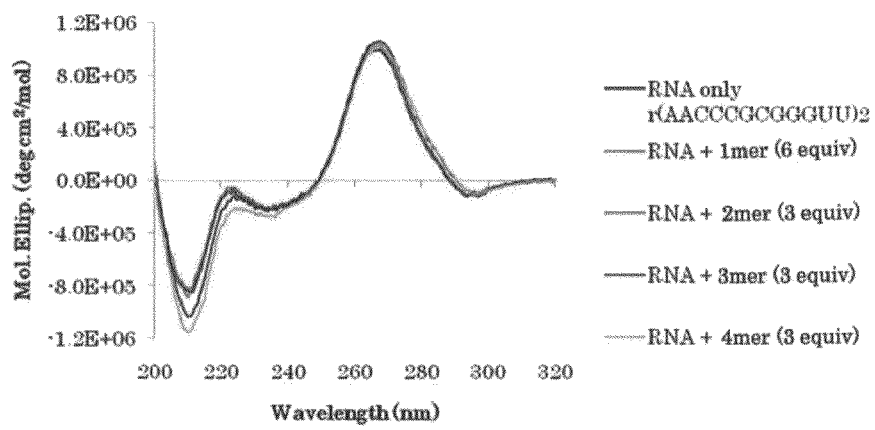
FIGS. 3A-B depict CD spectra of RNA (II) (SEQ ID NO: 7).
Figure 3:
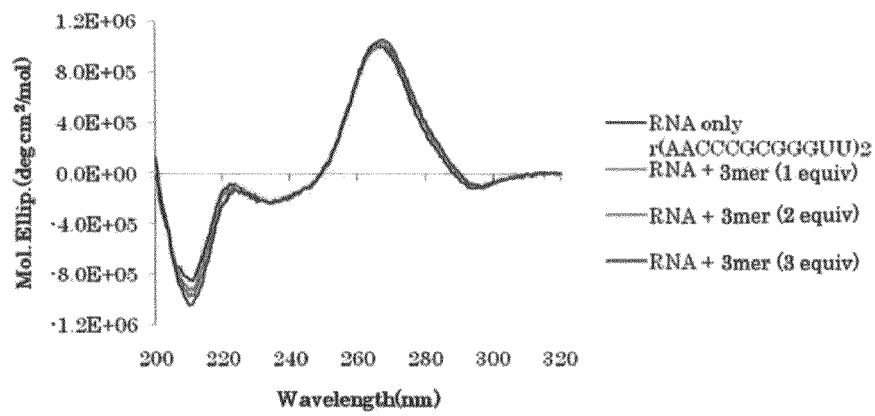

Similar measurements were performed for the CD spectrum of II. Change was scarcely observed in the systems added with the monosaccharide 43 and the disaccharide 45. Whilst in the systems added with the trisaccharide 42 and the tetrasaccharide 50, it was observed that the positive peak at around 265 nm slightly shifted by about 0.5 nm to the long wavelength side, and intensity of the peak at around 210 nm induced by the negative Cotton effect also increased by 25% and 30%, respectively, (FIG. 3, (A)). Then, changes caused by different equivalents of the trisaccharide 42 were observed (FIG. 3, (B)), and a result was obtained that each increase of equivalent gave corresponding increase of the peak intensity at around 210 nm. These results suggested that structural change of II caused by an oligo-diaminosaccharide was induced by adding the trisaccharide 42 and the tetrasaccharide 50. The changes in both I and II are considered to be slight as compared with the change of CD spectra caused by the change of the basal helical structure such as the change from the A-type to B-type. Therefore, these results suggest that the oligo-diaminosaccharides and the RNA double strands interacted and bound with small structural changes of the RNA double helices.

Figure 4:
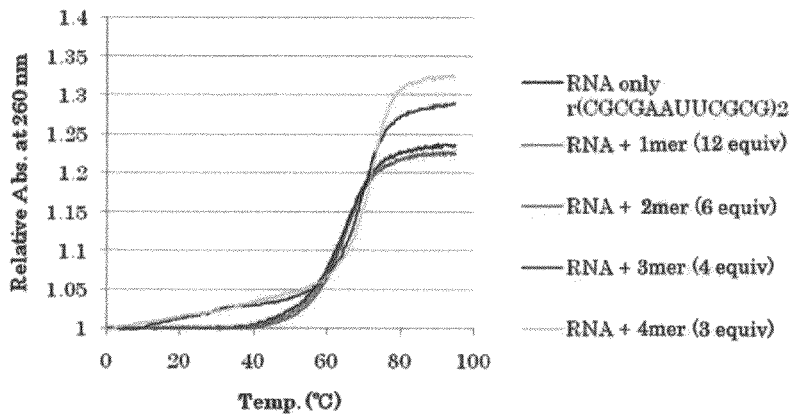
FIG. 4 depicts Tm curves of RNA (I) (SEQ ID NO: 6).

Tm curves are shown in FIG. 4. Although substantial changes of the Tm curves were not observed in the systems added with the monosaccharide 43 and the disaccharide 45, significant changes of the Tm curves were observed in the systems added with the trisaccharide 42 and the tetrasaccharide 50. In these systems, the value of Tm significantly increased by 4.1° C. when 4 equivalents of the trisaccharide 42 was added, and by 7.9° C. when 3 equivalents of the tetrasaccharide 50 were added, and moreover degree of the increase of the absorbance together with the increase of the temperature also markedly elevated. Therefore, comparison was performed for two kinds of factors, Tm and a degree of increase in absorbance. Tm curves were measured with the monosaccharide to tetrasaccharide, as well as neomycin and tobramycin, which are natural aminoglycoside antibiotics, and values of Tm calculated from the curves and thermal change ratios of absorbance are shown in Table 1. The values of Tm referred to in this specification are those calculated by the median line method, unless specifically indicated.

TABLE 1

|  |  | Abs(85° C.)/Abs(20° C.) | Tm/° C. | ΔTm/° C. |
|---|---|---|---|---|
| RNA only |  | 1.23 | 63.9 | — |
| 1mer | 12 eq | 1.22 | 63.9 | 0.0 |
| 2mer | 6 eq | 1.22 | 64.3 | 0.4 |
| 3mer | 1 eq | 1.22 | 65.3 | 1.4 |
|  | 2 eq | 1.23 | 66.8 | 2.9 |
|  | 3 eq | 1.23 | 67.3 | 3.4 |
|  | 4 eq | 1.27 | 69.0 | 5.1 |
| 4mer | 1 eq | 1.23 | 68.0 | 4.1 |
|  | 2 eq | 1.29 | 70.9 | 7.0 |
|  | 3 eq | 1.30 | 71.8 | 7.9 |
|  | 4 eq | 1.30 | 72.7 | 8.8 |
| neomycin | 1 eq | 1.23 | 66.9 | 3.0 |
|  | 2 eq | 1.24 | 67.9 | 4.0 |
|  | 3 eq | 1.27 | 68.8 | 4.9 |
|  | 4 eq | 1.28 | 69.4 | 5.5 |
| tobramycin | 1 eq | 1.24 | 64.9 | 1.0 |
|  | 2 eq | 1.22 | 65.0 | 1.1 |
|  | 3 eq | 1.22 | 65.7 | 1.8 |
|  | 4 eq | 1.25 | 66.2 | 2.3 |

As for Tm, higher melting points were observed when the saccharide chain lengths of the oligo-diaminosaccharides became longer. It is considered that a major factor of this result is that a longer saccharide chain length provides a larger number of amino groups per molecule, i.e., a larger number of phosphate moiety-binding sites per molecule. More specifically, the trisaccharide 42 and the tetrasaccharide 50 have lots of amino groups which can bind with phosphate moieties of RNA, and accordingly, the compounds can strongly bind to RNA due to cooperative effect at the time of binding, and thus can stabilize the double strand. As for the aminoglycoside antibiotics, focusing on the number of amino groups per molecule, it is considered that a major factor of the slight contribution of tobramycin to increase of Tm of I was the smaller number of amino groups per molecule thereof as compared to that of the trisaccharide 42. Neomycin gave stronger Tm-increasing effect as compared with the trisaccharide 42 although neomycin similarly has 6 amino groups in the molecule. This result suggests that neomycin, having four ring systems in the molecule and therefore the molecular length thereof is closer to the tetrasaccharide 50 rather than the trisaccharide 42, was advantageous for the fitting to the groove of I.

The ratio of change in absorbance also substantially corresponded to the change of the value of Tm, and higher ratio was observed when the saccharide chain lengths became longer, and increase of hypochromic effect was observed. These measurement results also corresponded to the changes in CD spectrum, and increase of Tm and hypochromic effect were observed for the trisaccharide 42, the tetrasaccharide 50, and neomycin, of which peak position at around 265 nm shifted. As a result, it was demonstrated that the oligo-diaminosaccharides interacted with the double strands with structural change and the structural change were accompanied with the increase of stacking of base pairs of nucleic acid, and thereby double strands were stabilized.

Figure 5:
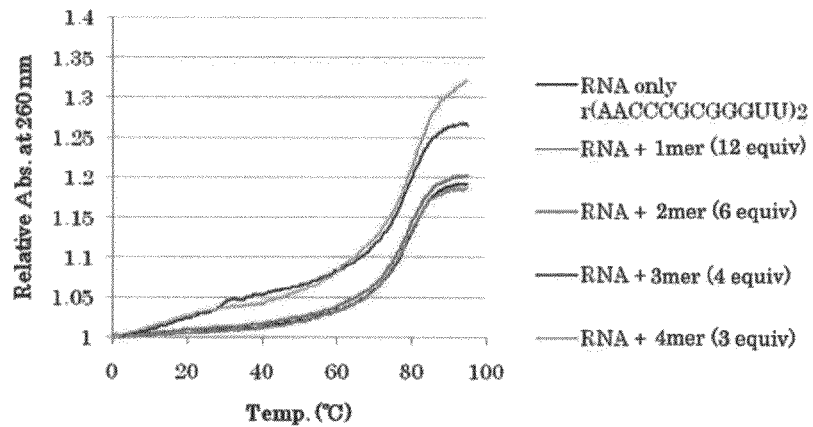
FIGS. 5A-B depict Tm curves of RNA (II) (SEQ ID NO: 7).
Figure 5:
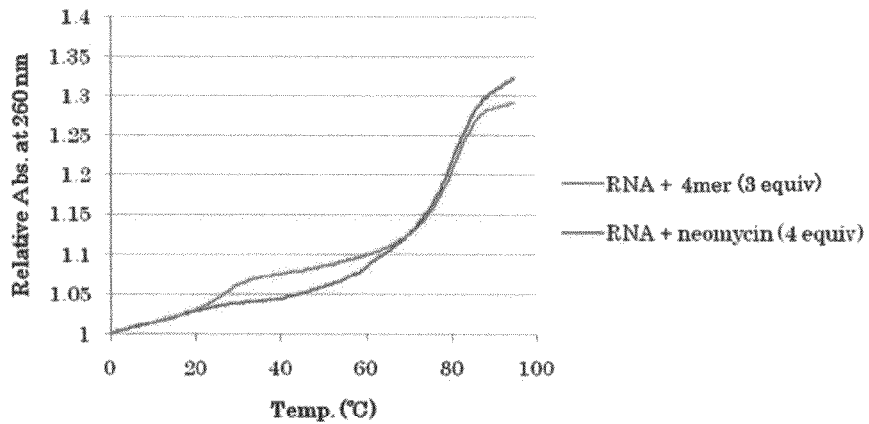

Also as for II, significant change of the Tm curve was observed in the system added with the tetrasaccharide 50 as shown in FIG. 5(A). As shown in FIGS. 5(A) and (B), almost no change in a ratio of temperature-dependent absorbance change was observed for the monosaccharide 43 and the disaccharide 45, and the ratio markedly increased as the saccharide chain length became longer from the trisaccharide 42 to the tetrasaccharide 50, and the above tendency was similar to that observed for I. The values of Tm are shown in Table 2.

TABLE 2

|  |  | Tm/° C. | ΔTm/° C. |
|---|---|---|---|
| RNA only |  | 77.7 | — |
| 1mer | 12 eq | 77.4 | −0.3 |
| 2mer | 6 eq | 77.5 | −0.2 |
| 3mer | 4 eq | 78.0 | 0.3 |
| 4mer | 1 eq | 77.9 | 0.2 |
|  | 2 eq | 78.3 | 0.6 |
|  | 3 eq | 79.6 | 1.9 |
|  | 4 eq | 80.2 | 2.5 |
| neomycin | 4 eq | 80.0 | 2.3 |
| tobramycin | 4 eq | 78.3 | 0.6 |

Although the tendency that a longer saccharide chain length more contributes to the increase of Tm was the same as that observed for I, degree of change of Tm was small in all the systems added with the mono- to tetrasaccharides, neomycin, and tobramycin. It is considered that this result is resulting from higher thermal stability of II of which Tm is 77.7° C. than I (Tm=63.9° C.), and thereby the oligo-diaminosaccharides and aminoglycosides more hardly contributed to stabilization of II. The change of Tm by the oligo-diaminosaccharides was remarkably smaller than that caused by the aminoglycosides. Almost no change of Tm was observed with the trisaccharide 42. Further, the increase of Tm induced by neomycin was slightly larger than the increase of Tm induced by the tetrasaccharide 50 under the same condition of equivalents of amino groups, and they were also comparable under the condition of 4 equivalents of the molecules.

Figure 6:
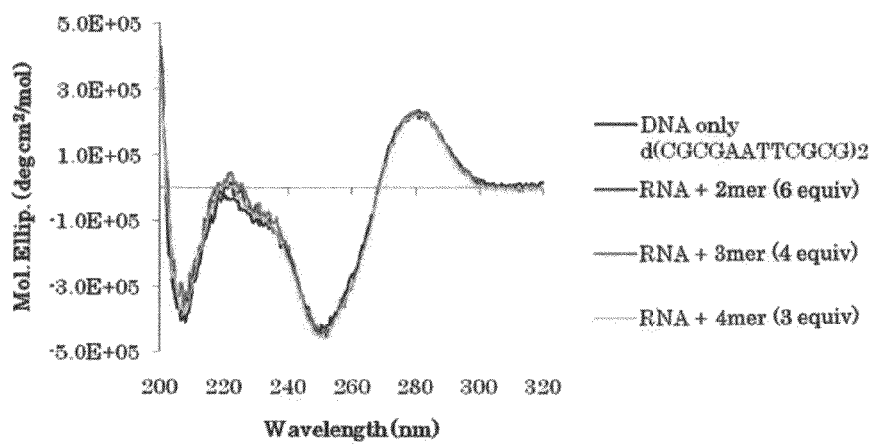
FIG. 6(A) depicts CD spectra of DNA (III) (SEQ ID NO: 8), and (B) depicts CD spectra of DNA (IV) (SEQ ID NO: 9).
Figure 6:
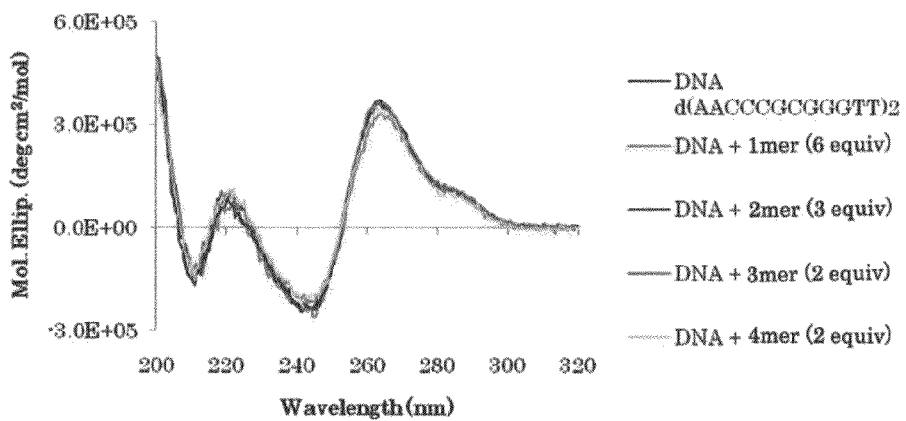

Then, interactions of the oligo-diaminosaccharides with d(CGCGAATTCGCG)$_2$ (SEQ ID NO: 8) (hereinafter referred to as III) and d(AACCCGCGGGTT)$_2$ (SEQ ID NO: 9) (hereinafter referred to as IV) as DNAs corresponding to the aforementioned RNAs I and II, respectively, were analyzed. The CD spectra of III are shown in FIG. 6(A). Neither shift of the peak position by the Cotton effect nor change of intensity was observed after the addition of the oligo-diaminosaccharides. This result indicates that structural change of the DNA double strand was not caused by the addition of the oligo-diaminosaccharides. The CD spectra of IV are shown in FIG. 6(B). Also in this case, significant change was not observed as in the case of III, and therefore it is considered that structural change of the DNA double strand was not caused.

Figure 7:
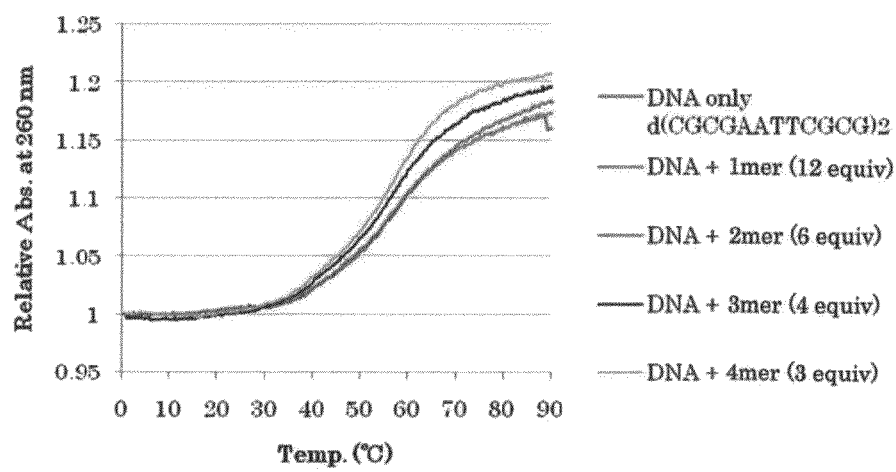
FIG. 7(A) depicts Tm curves of DNA (III) (SEQ ID NO: 8), and (B) depicts Tm curves of DNA (IV) (SEQ ID NO: 9).
Figure 7:
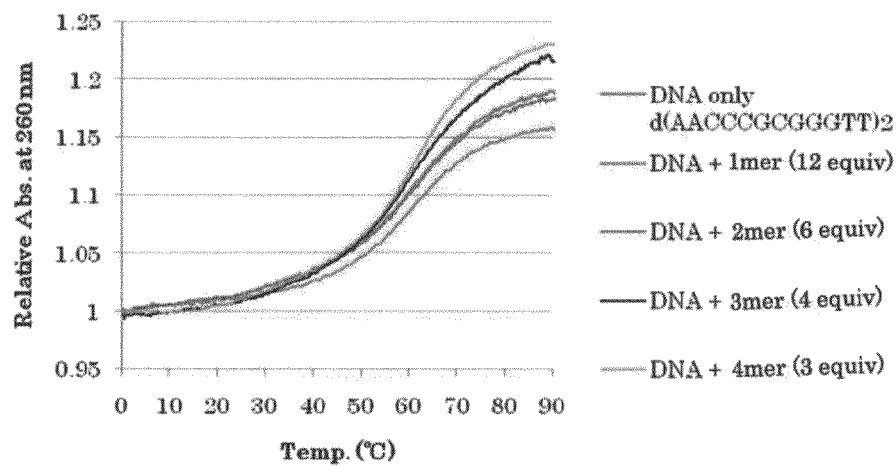

Tm curves of III and IV are shown in FIGS. 7(A) and (B), respectively. Although there was no significant change of Tm in both cases, significant increases of absorbance change ratio in the Tm curves were observed. These data are shown in Tables 3 and 4.

TABLE 3

|  |  | Abs(85° C.)/Abs(20° C.) | Tm/° C. | ΔTm/° C. |
|---|---|---|---|---|
| DNA only |  | 1.16 | 55.7 | — |
| 1mer | 12 eq | 1.16 | 55.4 | −0.3 |
| 2mer | 6 eq | 1.17 | 55.4 | −0.3 |
| 3mer | 4 eq | 1.20 | 55.3 | −0.4 |
| 4mer | 1 eq | 1.20 | 56.0 | 0.3 |
|  | 2 eq | 1.22 | 55.6 | −0.1 |
|  | 3 eq | 1.20 | 56.2 | 0.5 |
|  | 4 eq | 1.22 | 55.4 | −0.3 |
| neomycin | 1 eq | 1.18 | 54.9 | −0.8 |
|  | 2 eq | 1.19 | 55.1 | −0.6 |
|  | 3 eq | 1.20 | 55.4 | −0.3 |
|  | 4 eq | 1.20 | 55.7 | 0.0 |
| tobramycin | 1 eq | 1.17 | 54.8 | −0.9 |
|  | 2 eq | 1.18 | 55.3 | −0.4 |
|  | 3 eq | 1.18 | 55.3 | −0.4 |
|  | 4 eq | 1.18 | 54.5 | −1.2 |

TABLE 4

|  |  | Abs(85° C.)/Abs(20° C.) | Tm/° C. | ΔTm/° C. |
|---|---|---|---|---|
| DNA only |  | 1.17 | 60.4 | — |
| 1mer | 12 eq | 1.14 | 60.0 | −0.4 |
| 2mer | 6 eq | 1.17 | 60.3 | −0.1 |
| 3mer | 4 eq | 1.20 | 60.1 | −0.3 |
| 4mer | 1 eq | 1.22 | 60.0 | −0.4 |
|  | 2 eq | 1.23 | 60.4 | 0.0 |
|  | 3 eq | 1.22 | 60.4 | 0.0 |
|  | 4 eq | 1.25 | 60.5 | 0.1 |
| neomycin | 4 eq | 1.18 | 60.1 | −0.3 |
| tobramycin | 4 eq | 1.16 | 60.1 | −0.3 |

It was confirmed that a certain degree of increase of the hypochromic effect was provided for both of the DNA sequences of III and IV. No change was observed in the stability and structure of the double strands, suggesting almost no possibility of interaction of the oligo-diaminosaccharides with the double strands. Accordingly, it is considered that they interacted with DNAs dissociated into single strands to inhibit interactions of bases of nucleic acid in the single-stranded DNA and thereby increased the absorbance in the high temperature region.

Figure 8:
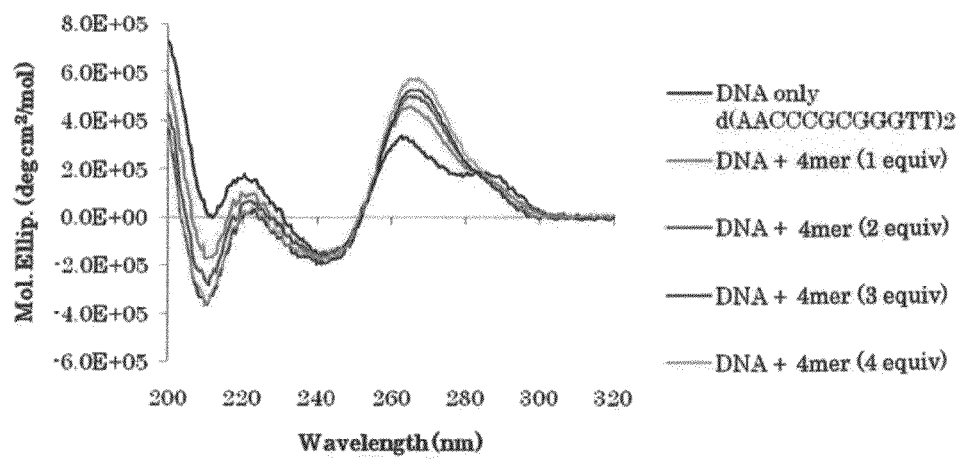
FIG. 8(A) depicts CD spectra of DNA (IV) (SEQ ID NO: 9) (0 mM NaCl), and (B) depicts Tm curves of DNA (IV) (SEQ ID NO: 9) (0 mM NaCl).
Figure 8:
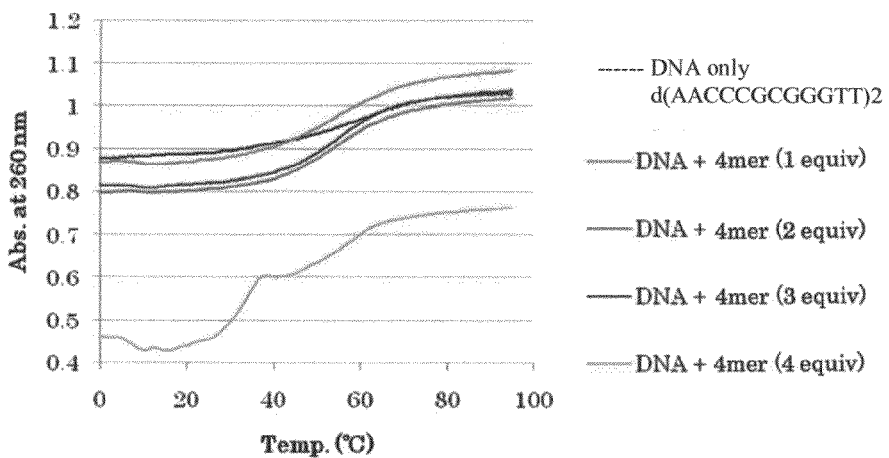

Similar experiments were performed for IV at low salt concentrations as conditions under which electrostatic interactions can more strongly occur. The experiments were performed with changing the concentration of sodium chloride from 100 mM to 0 mM, without changing the concentration of the phosphate buffer and pH of the solution (FIG. 8(A)). In the CD spectra, positive peaks were observed at around 280 nm as well as at around 265 nm, suggesting the presence of a structure different from that formed at 100 mM sodium chloride. In the Tm measurement under this condition, the Tm curve did not give definite inflexion point (FIG. 8(B)). On the basis of these results, it is considered that, at a low salt concentration, DNAs do not have a single double helix structure, but have two or more kinds of structures in an intermingled state.

It was found that if the oligo-diaminosaccharides were added, the positive peak at around 280 nm became smaller in the CD spectrum. When the trisaccharide 42 and the tetrasaccharide 50 were added, this peak substantially disappeared, and the Tm curves came to give a definite inflexion point, i.e., Tm. Moreover, profiles of the CD spectra obtained by adding the oligo-diaminosaccharides were similar to that of the spectrum of DNA obtained in the presence of 100 mM sodium chloride (FIG. 6(B)). These results indicated that, when the oligo-diaminosaccharides were added to DNAs which did not have a single structure at a low salt concentration, DNAs came to take a single double helix structure similar to that observed under a physiological condition. Further, in the system added with 4 equivalents of the tetrasaccharide 50, extreme reduction of absorbance was observed at a low temperature in the Tm measurement. The above result indicates that one oligo-diaminosaccharide binds with nucleobases of two or more DNAs to form aggregates.

Figure 9:
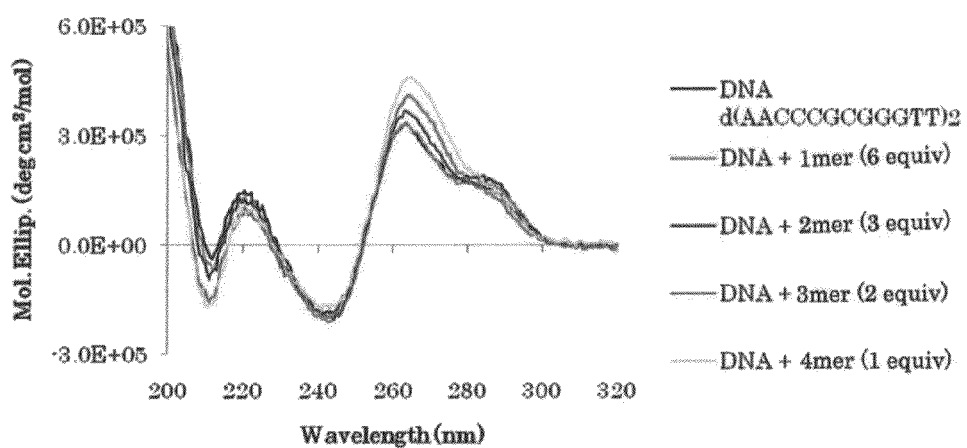
FIG. 9 depicts CD spectra of DNA (IV) (SEQ ID NO: 9) (0 mM NaCl).

The CD spectra observed after addition of the mono- to trisaccharides having a short saccharide chain length are shown in FIG. 9. A change similar to that observed after the addition of the tetrasaccharide 50 was also observed with the addition of the disaccharide 45 and the trisaccharide 42, but degree of the change was small. Furthermore, change was not observed in the system added with the monosaccharide 43. These results indicate that formation of double helix of DNA caused by the oligo-diaminosaccharides was not induced only as a result of the increase of the salt concentration. More specifically, it is suggested that a cooperative effect was observed in that the DNAs, not forming double helices at a low salt concentration, can be made to form a helical structure similarly under a physiological condition by adding an oligo-diaminosaccharide having a long chain length.

As described above, it was found that the oligo-diaminosaccharides, especially the trisaccharide 42 and the tetrasaccharide 50, interacted with RNA double strands to induce structural change, and thereby improve the stability. On the other hand, no interaction with DNA double strands inducing increase of Tm or structural change was observed under the same condition.

Example 3

Interactions with RNA double strands and DNA/RNA double strands were examined in the same manner as that of Example 2. In the following examples, RNA strands are indicated with a heading symbol "r", and DNA strands are indicated with a heading symbol "d". For example, $(rA_6U_6)_2$ (SEQ ID NO: 1) represents $5'rA_6U_63'/5'rA_6U_63'$ (SEQ ID NO: 1).

Figure 10:
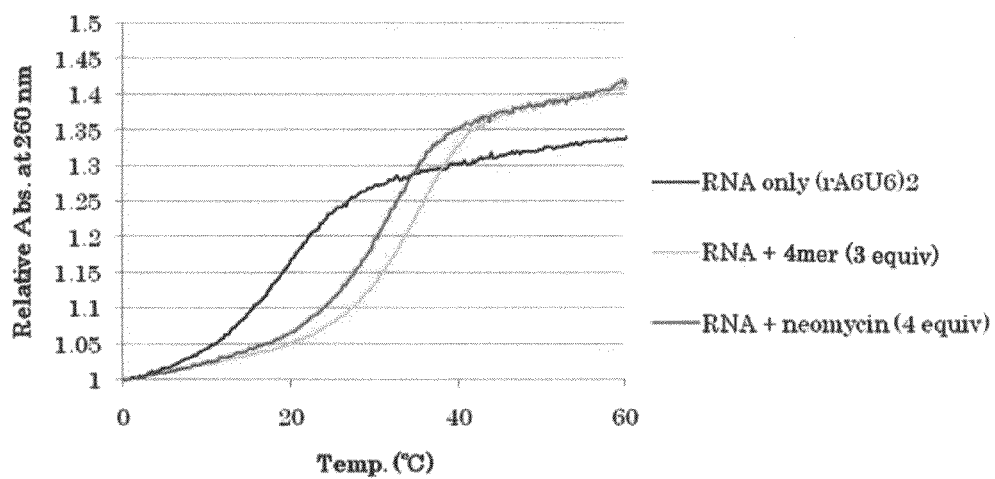
FIG. 10 depicts Tm curves of a 12-mer RNA/RNA double strand (5'$rA_6U_6$3'/5'$rA_6U_6$3' (SEQ ID NO: 1)).
Figure 11:
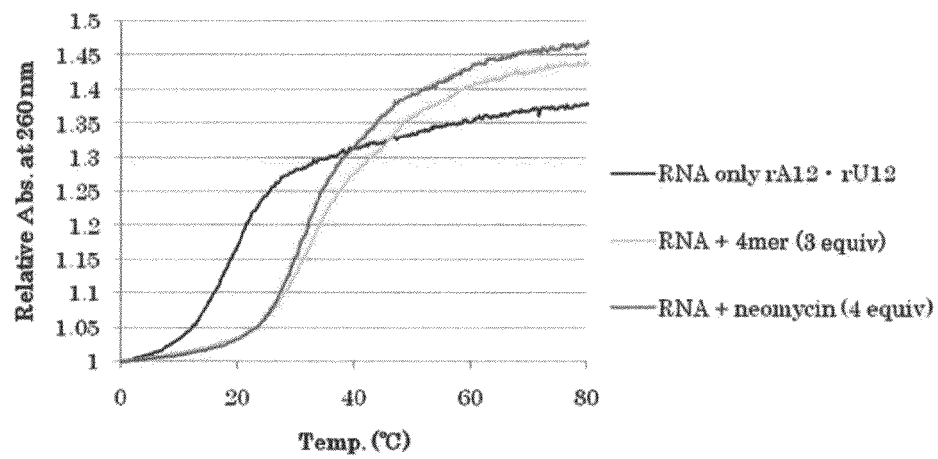
FIG. 11 depicts Tm curves of a 12-mer RNA/RNA double strand (5'$rA_{12}$3'/5'$rU_{12}$3' (SEQ ID NO: 2)).
Figure 12:
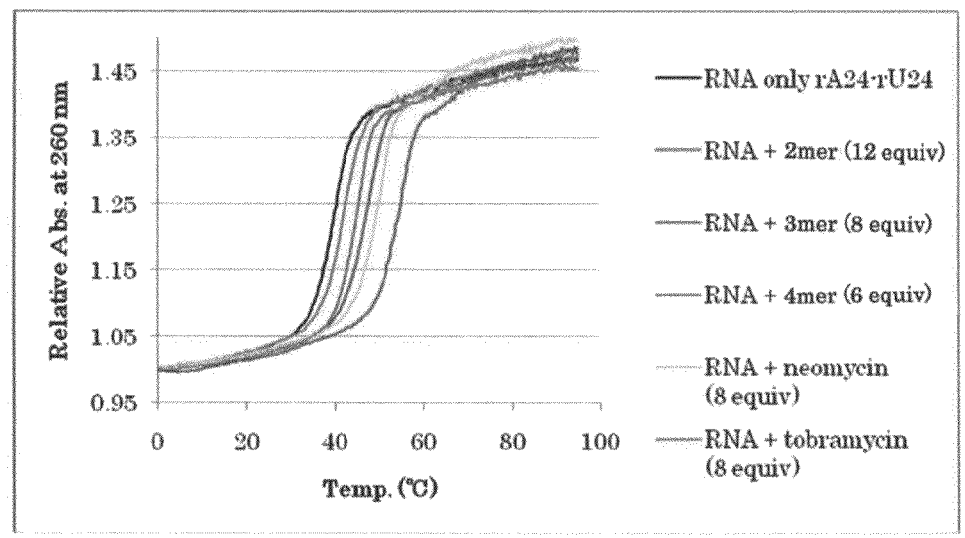
FIG. 12 depicts Tm curves of a 24-mer RNA/RNA double strand (5'$rA_{24}$3'/5'$rU_{24}$3' (SEQ ID NO: 3)).

The Tm curves and absorbance change ratios in the Tm curves of a 12-mer RNA/RNA double strand ($5'rA_6U_63'/5'rA_6U_63'$ (SEQ ID NO: 1)) are shown in FIG. 10 and Table 5. RNA double strands consisting only of A and U have a low melting point, and accordingly, a marked increase of Tm was induced by the addition of the oligo-diaminosaccharide of the present invention. In FIG. 11 and Table 6, the Tm curves and absorbance change ratios in the Tm curves of a 12-mer RNA/RNA double strand ($5'rA_{12}3'/5'rU_{12}3'$ (SEQ ID NO: 2)) are shown. Also for the RNA/RNA double strand ($5'rA_{12}3'/5'rU_{12}3'$ (SEQ ID NO: 2)), results similar to those for the RNA/RNA double strand ($5'rA_6U_63'/5'rA_6U_63'$ (SEQ ID NO: 1)) were obtained. In FIG. 12 and Table 7, the Tm curves and absorbance change ratios in the Tm curves of a 24-mer RNA/RNA double strand ($5'rA_{24}3'/5'rU_{24}3'$ (SEQ ID NO: 3)) are shown. Also for the 24-mer RNA/RNA double strand, increase of Tm induced by the addition of the oligo-diaminosaccharides was observed as in the case of the 12-mer RNA/RNA double strands.

TABLE 5

|  |  | Abs(60° C.)/Abs(0° C.) | Tm/° C. | ΔTm/° C. |
|---|---|---|---|---|
| RNA only |  | 1.35 | 19.0 | — |
| 4mer | 3 eq | 1.41 | 35.3 | 16.3 |
| neomycin | 4 eq | 1.41 | 32.6 | 13.6 |

TABLE 6

|  |  | Abs(60° C.)/Abs(0° C.) | Tm/° C. | ΔTm/° C. |
|---|---|---|---|---|
| RNA only |  | 1.35 | 18.8 | — |
| 2mer | 6 eq | 1.39 | 22.2 | 3.4 |
| 3mer | 4 eq | 1.38 | 30.5 | 11.7 |
| 4mer | 3 eq | 1.41 | 35.2 | 16.4 |
| neomycin | 4 eq | 1.43 | 33.3 | 14.5 |
| tobramycin | 4 eq | 1.39 | 25.2 | 6.4 |

TABLE 7

|  |  | Abs(85° C.)/Abs(20° C.) | Tm/° C. | ΔTm/° C. |
|---|---|---|---|---|
| RNA only |  | 1.42 | 39.3 | — |
| 2mer | 12 eq | 1.43 | 41.8 | 2.5 |
| 3mer | 8 eq | 1.42 | 46.8 | 7.5 |
| 4mer | 6 eq | 1.45 | 54.5 | 15.2 |
| neomycin | 8 eq | 1.45 | 49.7 | 10.4 |
| tobramycin | 8 eq | 1.42 | 44.5 | 5.2 |

Figure 13:
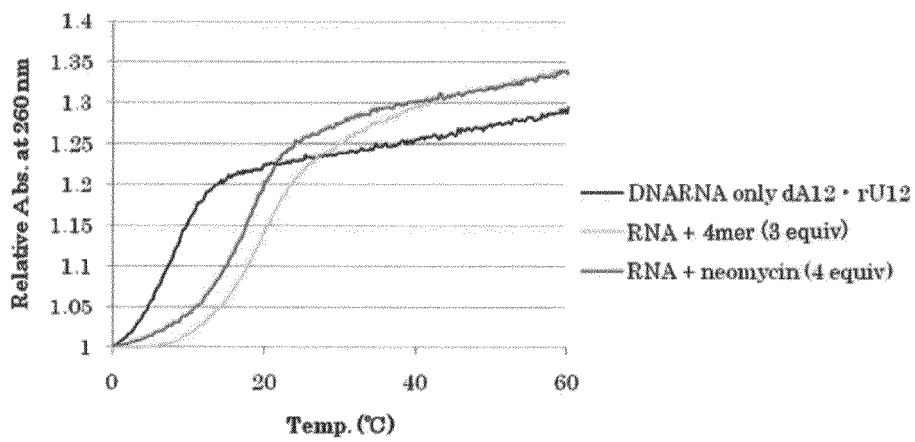
FIG. 13 depicts Tm curves of a 12-mer DNA/RNA double strand (5'$dA_{12}$3'/5'$rU_{12}$3' (SEQ ID NO: 4)).

The Tm curves and absorbance change ratios in the Tm curves of a 12-mer DNA/RNA double strand ($5'dA_{12}3'/5'rU_{12}3'$ (SEQ ID NO: 4)) are shown in FIG. 13 and Table 8. Increase of Tm was also observed for the DNA/RNA double strand. Degree of the increase of Tm was smaller than that observed for the RNA double strands. This DNA/RNA double strand has a low Tm, and accordingly, Tm was calculated by differentiation and thermal change ratio of absorbance was not calculated.

TABLE 8

|  |  | Tm/° C. | ΔTm/° C. |
|---|---|---|---|
| DNA-RNA only |  | 11.9 | — |
| 4mer | 3 eq | 20.0 | 8.1 |
| neomycin | 4 eq | 18.2 | 6.3 |

Figure 14:
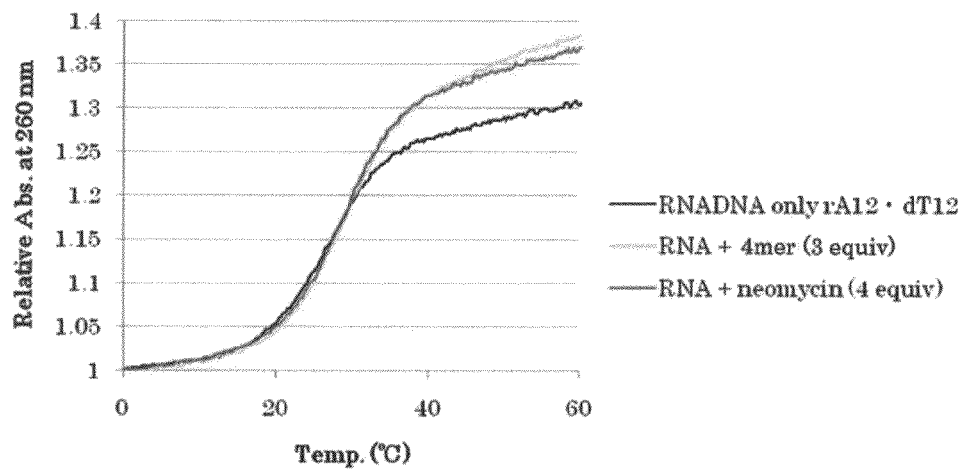
FIG. 14 depicts Tm curves of a 12-mer RNA/DNA double strand (5'$rA_{12}$3'/5'$dT_{12}$3' (SEQ ID NO: 2)).

The Tm curves and absorbance change ratios in the Tm curves of a 12-mer RNA/DNA double strand ($5'rA_{12}3'/5'dT_{12}3'$ (SEQ ID NO: 2)) are shown in FIG. 14 and Table 9. Increase of Tm was also observed for the RNA/DNA double strand. An RNA consisting of homopurine gave a higher Tm as compared with an RNA strand consisting of homopyrimidine, indicating increase of Tm induced by the addition of the oligo-diaminosaccharide was small.

TABLE 9

|  |  | Abs(60° C.)/Abs(0° C.) | Tm/° C. | ΔTm/° C. |
|---|---|---|---|---|
| RNA-DNA only | | 1.30 | 26.6 | — |
| 4mer | 3 eq | 1.38 | 29.4 | 2.8 |
| neomycin | 4 eq | 1.37 | 28.7 | 2.1 |

Figure 15:
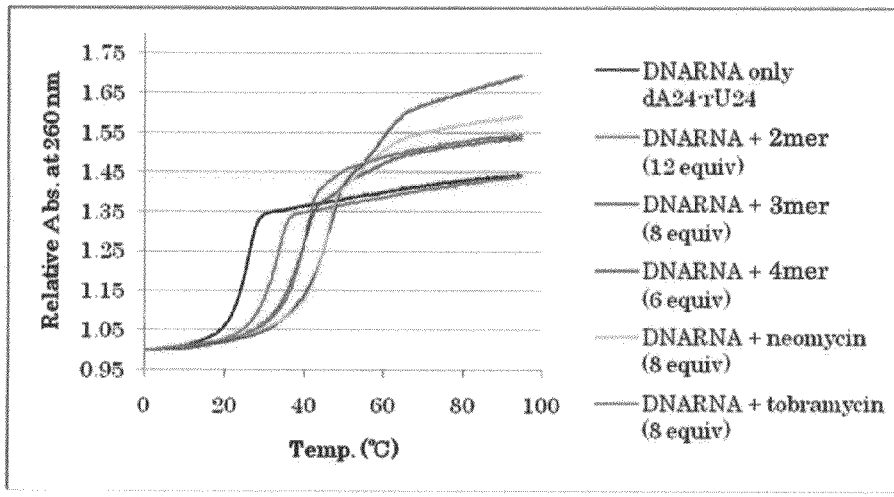
FIG. 15 depicts Tm curves of a 24-mer DNA/RNA double strand (5'$dA_{24}$3'/5'$rU_{24}$3' (SEQ ID NO: 5)).

The Tm curves and absorbance change ratios in the Tm curves of a 24-mer DNA/RNA double strand (5'dA$_{24}$3'/5'rU$_{24}$3' (SEQ ID NO: 5)) are shown in FIG. 15 and Table 10. Tm of this DNA/RNA double strand, having the chain length twice as long as that of 12-mer, was remarkably increased.

TABLE 10

|  |  | Abs(70° C.)/Abs(0° C.) | Tm/° C. | ΔTm/° C. |
|---|---|---|---|---|
| DNARNA only | | 1.42 | 24.9 | — |
| 2mer | 12 eq | 1.40 | 32.0 | 7.1 |

TABLE 10-continued

|  |  | Abs(70° C.)/Abs(0° C.) | Tm/° C. | ΔTm/° C. |
|---|---|---|---|---|
| 3mer | 8 eq | 1.50 | 39.6 | 14.7 |
| 4mer | 6 eq | 1.62 | 46.7 | 21.8 |
| neomycin | 8 eq | 1.55 | 45.8 | 20.8 |
| tobramycin | 8 eq | 1.51 | 39.7 | 14.7 |

Figure 16:
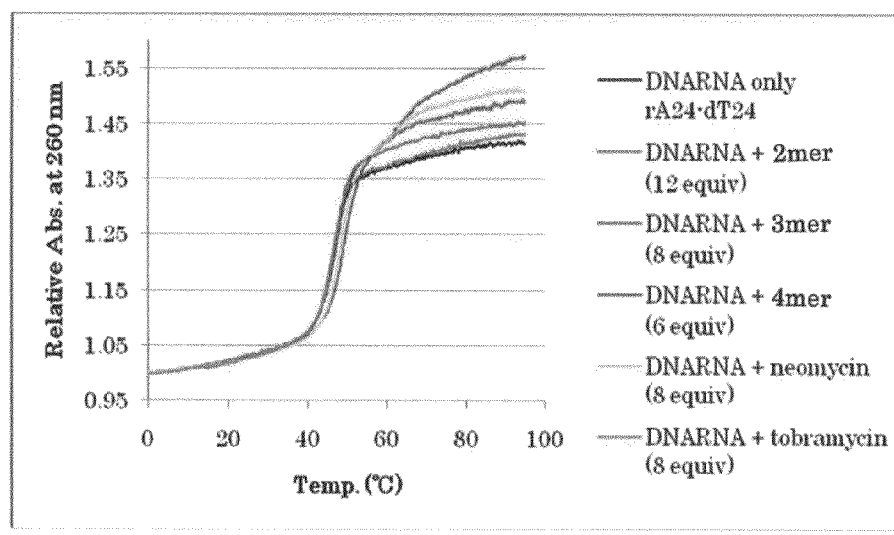
FIG. 16 depicts Tm curves of a 24-mer RNA/DNA double strand (5'$rA_{24}$3'/5' $dT_{24}$3' (SEQ ID NO: 3)).

In the same manner, the Tm curves and absorbance change ratios in the Tm curves of a 24-mer RNA/DNA double strand (5'rA$_{24}$3'/5'dT$_{24}$3' (SEQ ID NO: 3)) are shown in FIG. 16 and Table 11.

TABLE 11

|  |  | Abs(80° C.)/Abs(0° C.) | Tm/° C. | ΔTm/° C. |
|---|---|---|---|---|
| DNARNA only | | 1.41 | 46.2 | — |
| 2mer | 12 eq | 1.42 | 46.2 | 0.0 |
| 3mer | 8 eq | 1.47 | 47.5 | 1.3 |
| 4mer | 6 eq | 1.53 | 50.2 | 4.0 |
| neomycin | 8 eq | 1.49 | 48.9 | 2.7 |
| tobramycin | 8 eq | 1.44 | 46.8 | 0.6 |

What is claimed is:

1. A compound represented by the following general formula (I):

$$R^1\text{—}O\text{—}(X)n\text{-}R^2 \qquad (I)$$

wherein $R^1$ represents hydrogen atom or a monovalent substituent, $R^2$ represents hydrogen atom or a monovalent substituent, n represents an integer of 3 to 6, and X may be the same or different, and are independently selected from the divalent groups represented by the following formulas (a) to (i):

[Formula 1]

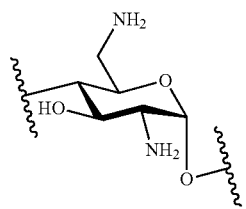
(a)

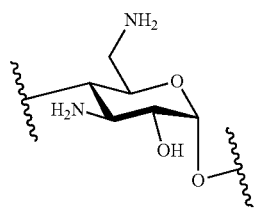
(b)

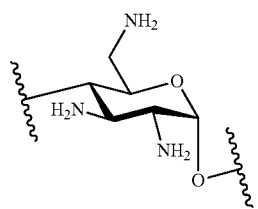
(c)

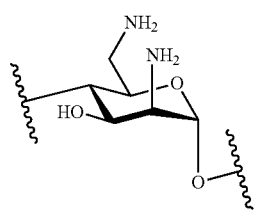
(d)

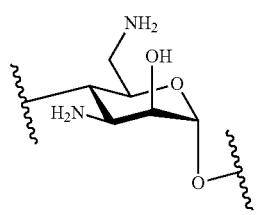
(e)

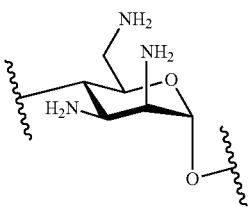
(f)

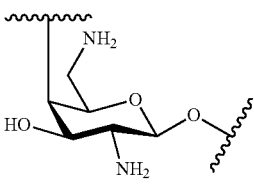
(g)

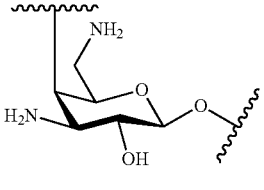
(h)

(i)

or a salt thereof.

2. The compound or a salt thereof according to claim 1, wherein $R^1$ is hydrogen atom, and $R^2$ is hydrogen atom or an alkyl group which may have a substituent.

3. The compound or a salt thereof according to claim 1, wherein X is a divalent group represented by any one of the formulas (a) to (f).

4. The compound or a salt thereof according to claim 1, wherein X are all the divalent group represented by the formula (a).

5. An agent for stabilizing an A-type double-stranded nucleic acid, which comprises the compound represented by the general formula (I) or a salt thereof according to claim 1.

6. An agent for selectively binding to an A-type double-stranded nucleic acid, which comprises the compound represented by the general formula (I) or a salt thereof according to claim 1.

7. A complex of the compound represented by the general formula (I) or a salt thereof according to claim 1 and an A-type double-stranded nucleic acid.

* * * * *